US010357546B2

(12) United States Patent
Chang et al.

(10) Patent No.: US 10,357,546 B2
(45) Date of Patent: Jul. 23, 2019

(54) ACCELERATION OF DIABETIC WOUND HEALING

(71) Applicant: University of Notre Dame du Lac, South Bend, IN (US)

(72) Inventors: Mayland Chang, Granger, IN (US); Shahriar Mobashery, Granger, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 15/512,148

(22) PCT Filed: Sep. 21, 2015

(86) PCT No.: PCT/US2015/051252
§ 371 (c)(1),
(2) Date: Mar. 17, 2017

(87) PCT Pub. No.: WO2016/044844
PCT Pub. Date: Mar. 24, 2016

(65) Prior Publication Data
US 2017/0274053 A1    Sep. 28, 2017

Related U.S. Application Data

(60) Provisional application No. 62/128,871, filed on Mar. 5, 2015, provisional application No. 62/052,921, filed on Sep. 19, 2014.

(51) Int. Cl.
| | |
|---|---|
| *A61K 38/43* | (2006.01) |
| *A61K 9/00* | (2006.01) |
| *A61L 15/44* | (2006.01) |
| *A61K 47/02* | (2006.01) |
| *A61K 47/06* | (2006.01) |
| *A61K 9/06* | (2006.01) |
| *A61K 9/12* | (2006.01) |
| *A61K 9/20* | (2006.01) |
| *A61K 9/48* | (2006.01) |
| *A61K 38/17* | (2006.01) |

(52) U.S. Cl.
CPC ............ *A61K 38/43* (2013.01); *A61K 9/0014* (2013.01); *A61K 9/0019* (2013.01); *A61K 9/06* (2013.01); *A61K 9/12* (2013.01); *A61K 9/2054* (2013.01); *A61K 9/4866* (2013.01); *A61K 38/17* (2013.01); *A61K 47/02* (2013.01); *A61K 47/06* (2013.01); *A61L 15/44* (2013.01); *A61L 2300/434* (2013.01)

(58) Field of Classification Search
CPC ...................................................... A61K 38/43
See application file for complete search history.

(56) References Cited

U.S. PATENT DOCUMENTS

| | | | |
|---|---|---|---|
| 6,020,181 A | 2/2000 | Bini | |
| 6,025,150 A | 2/2000 | Livant | |
| 6,166,084 A | 12/2000 | Bloor | |
| 6,555,118 B1 | 4/2003 | Niazi | |
| 6,600,057 B2 | 7/2003 | Quirk | |
| 6,703,415 B2 * | 3/2004 | Mobashery | C07D 303/34 514/430 |
| 7,144,917 B2 * | 12/2006 | Mobashery | C07D 303/34 514/430 |
| 7,320,783 B2 | 1/2008 | Livant | |
| 7,402,571 B2 | 7/2008 | Tennenbaum et al. | |
| 7,727,520 B2 | 6/2010 | Ferguson | |
| 7,879,798 B1 | 2/2011 | Aufseeser | |
| 7,928,127 B2 * | 4/2011 | Lee | C07D 303/34 514/336 |
| 7,981,426 B2 | 7/2011 | Kim | |
| 7,993,665 B2 | 8/2011 | Colin et al. | |
| 8,012,947 B2 | 9/2011 | Tomic et al. | |
| 8,093,287 B2 * | 1/2012 | Lee | C07D 303/34 514/430 |
| 8,129,341 B2 | 3/2012 | Gold et al. | |
| 8,247,384 B2 | 8/2012 | Green et al. | |
| 8,937,151 B2 * | 1/2015 | Chang | C07D 331/02 530/300 |
| 9,321,754 B2 * | 4/2016 | Chang | C07D 331/02 |
| 9,604,957 B2 * | 3/2017 | Chang | C07D 413/12 |
| 9,867,805 B2 * | 1/2018 | Chang | C07D 331/02 |
| 9,951,035 B2 * | 4/2018 | Chang | C07D 413/12 |
| 2006/0125208 A1 | 6/2006 | Nejsum | |
| 2007/0232541 A1 | 10/2007 | Reiter et al. | |
| 2009/0068251 A1 | 3/2009 | Tomic et al. | |
| 2011/0293643 A1 | 12/2011 | Wilkes | |

(Continued)

FOREIGN PATENT DOCUMENTS

WO    2011026107 A1    3/2011

OTHER PUBLICATIONS

Gooyit et al. J. Med. Chem. 2013, 56, 8139-8150 (Year: 2013).*
Korpi et al. British Journal of Cancer 2008, 98, 766-775 (Year: 2008).*
Armstrong, et al., "The Role of Matrix Metalloproteinases in Wound Healing", J Am Podiatr Med Assoc., 92(1):12-18, Jan. 2002.
Brown et al., "Potent and Selective Mechanism-Based Inhibition of Gelatinases," J. Am. Chem. Soc., 122:6799-6800, Jun. 2000.
Chen et al., "Molecular and mechanistic validation of delayed healing rat wounds as a model for human chronic wounds," Wound Repair Regen., 7(6):486-494, Nov.-Dec. 1999.
Fisher et al. "Recent Advances in MMP inhibitor design," Cancer Metastasis Rev., 25(1):115-136, Mar. 2006.

(Continued)

*Primary Examiner* — Matthew P Coughlin
(74) *Attorney, Agent, or Firm* — Haukaas Fortius PLLC; Michael H. Haukaas

(57) ABSTRACT

The invention provides compounds, compositions, and methods to improve or accelerate the healing of a wound. In various embodiments, the methods can include the topical treatment of the wound with the enzyme MMP-8, or the topical treatment of the wound with MMP-8 in combination with administration of an MMP-9 inhibitor, to accelerate the healing of the wound.

20 Claims, 12 Drawing Sheets

(56) References Cited

U.S. PATENT DOCUMENTS

2012/0052110 A1 3/2012 Tomic et al.

OTHER PUBLICATIONS

Gooyit, M., et al., "A Chemical Biological Strategy to Facilitate Diabetic Wound Healing," ACS Chem Biol.,9(1):105-110, Jan. 2014.
Gutierrez-Fernandez, et al., "Increased Inflammation Delays Wound Healing in Mice Deficient in Collagenase-2 (MMP-8)," The FASEB Journal 21(10):2580-2591, Aug. 2010.
Harsha, et al., "ADAM12: a Potential Target for the Treatment of Chronic Wounds," J Mol Med (Berl)., 86(8):961-969, Aug. 2008.
Hesek et al., "Design and Characterization of a Metalloproteinase Inhibitor-Tethered Resin for the Detection of Active MMPs in Biological Samples", Chem Biol., 13(4):379-386, Apr. 2006.
Hesek, et al., "Synthesis of an Inhibitor-Tethered Resin for Detection of Active Matrix Metalloproteinases Involved in Disease," J.Org.Chem., 71(16): 5848-5854, Jul. 2006.
International Search Report and written Opinion of the ISA/US in Int'l Application No. PCT/US2015/051252, dated Jan. 7, 2016, 7pgs.
Pradhan, et al. "Wound Healing Abnormalities in Diabetes and New Therapeutic Interventions", Diabetic Foot, pp. 68-72 (2007).
Toth, et al., "Tissue Inhibitor of Metalloproteinase (TIMP)-2 Acts Synergistically with Synthetic Matrix Metalloproteinase(MMP) Inhibitors but Not with TIMP-4 to Enhance the (Membrane Type1 )-MMP-dependent Activation of Pro-MMP-2*," J Biol Chem. 0, 275(52):41415-41423, Dec. 2000.
Zhang et al., "Role of Matrix Metalloproteinases and Therapeutic Benefits of Their Inhibition in Spinal Cord Injury," Neurotherapeutics, (2):206-220, Apr. 2011.

* cited by examiner

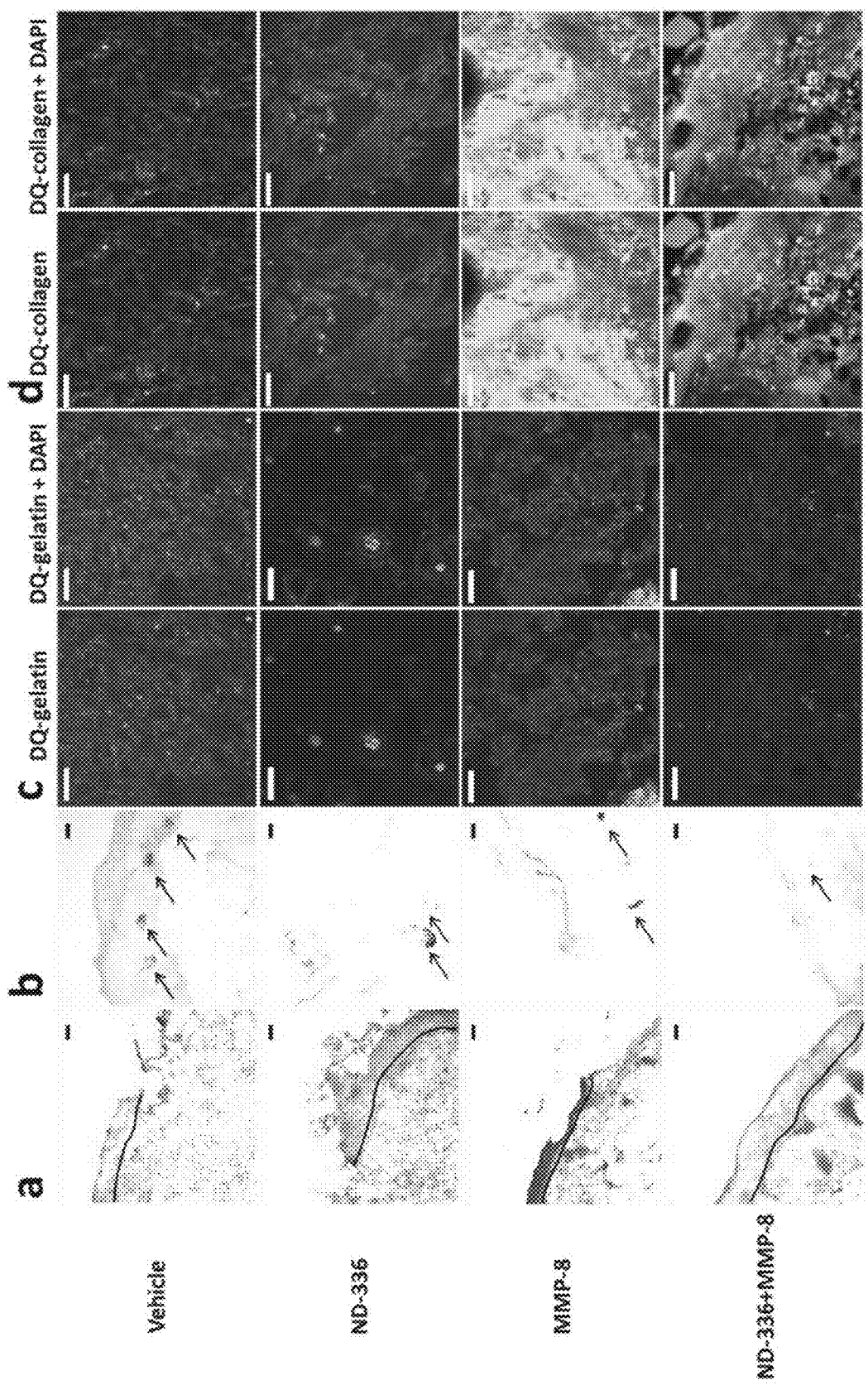
Fig. 2A-D

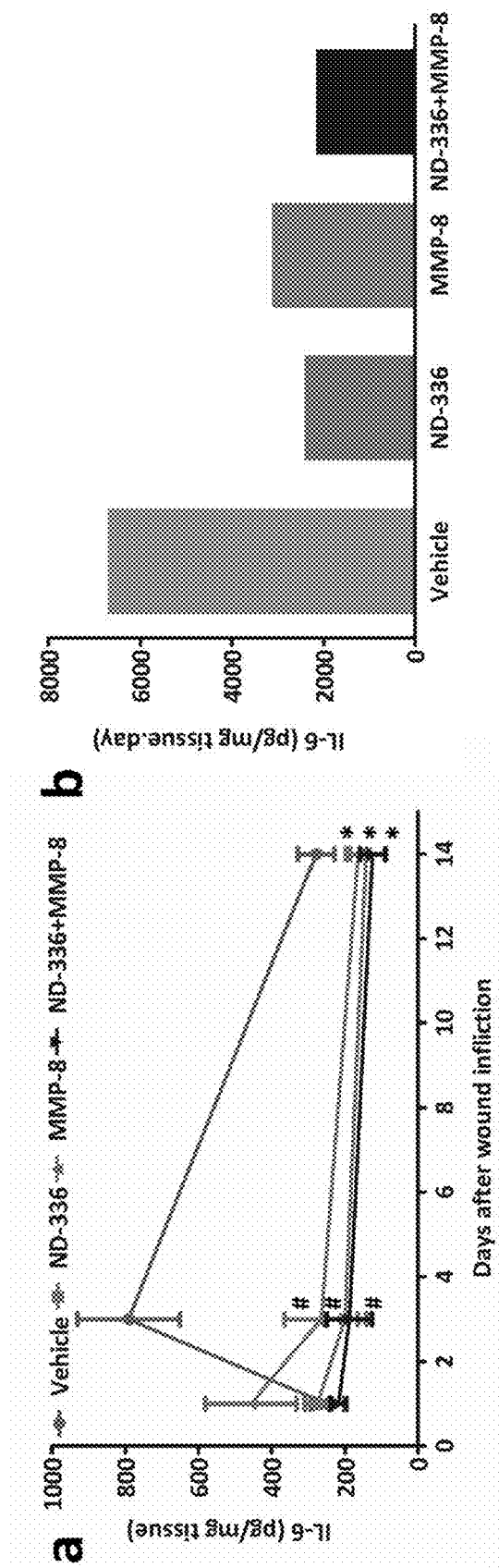
Fig. 3A-B

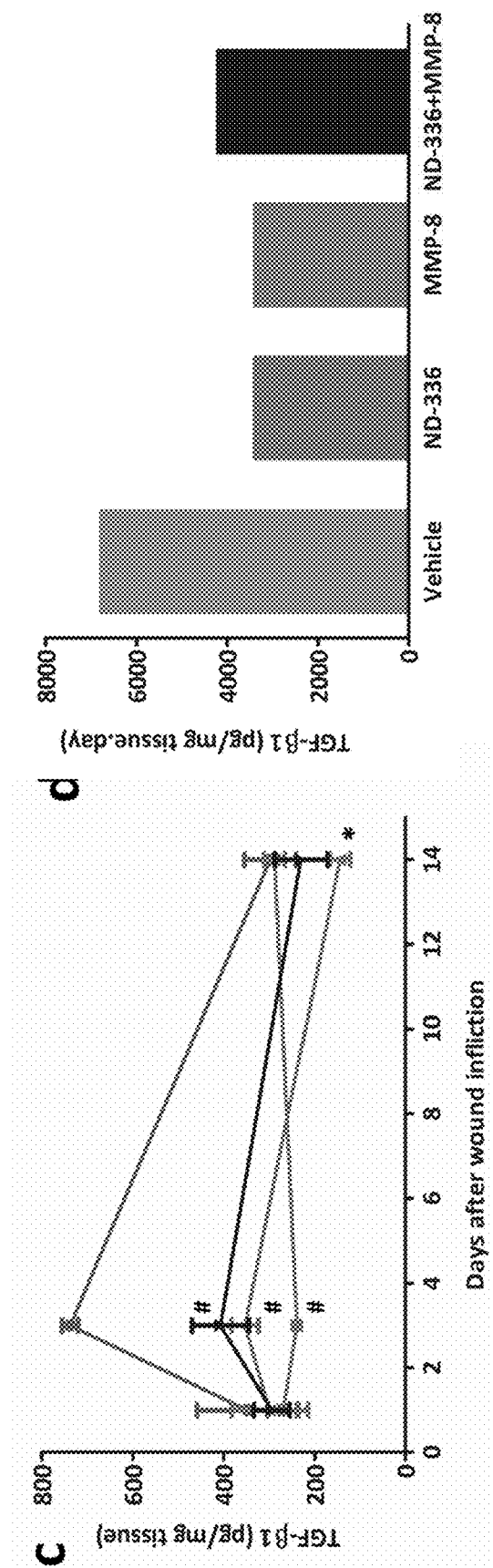
Fig. 3C-D

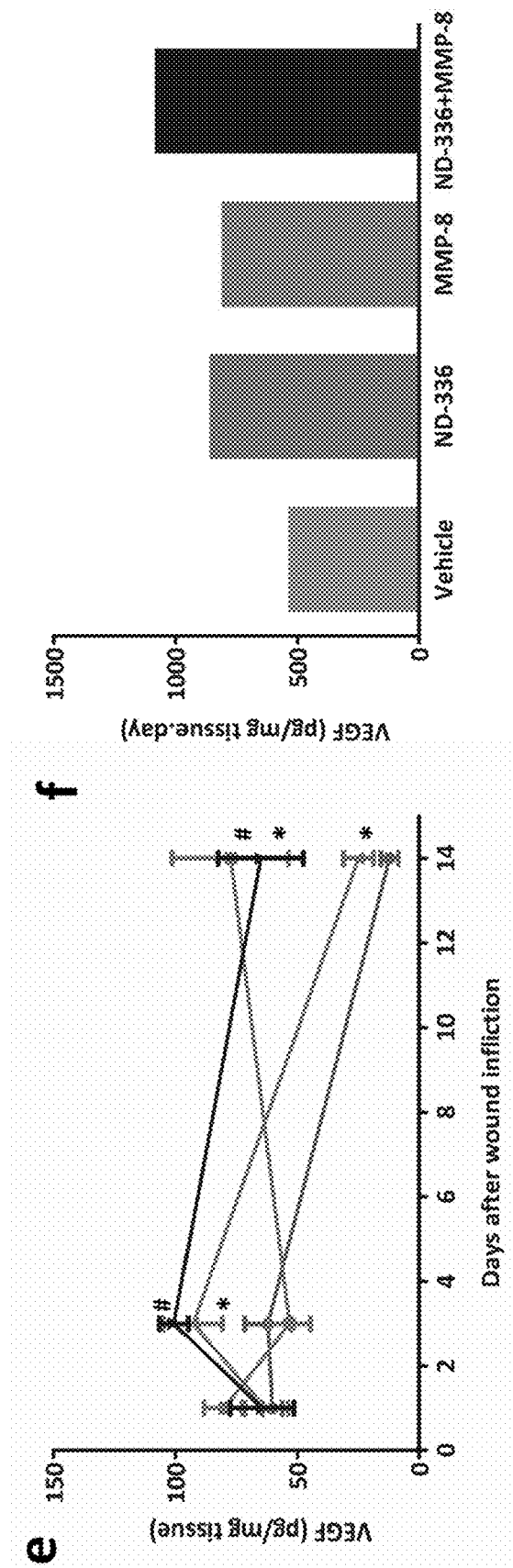
Fig. 3E-F

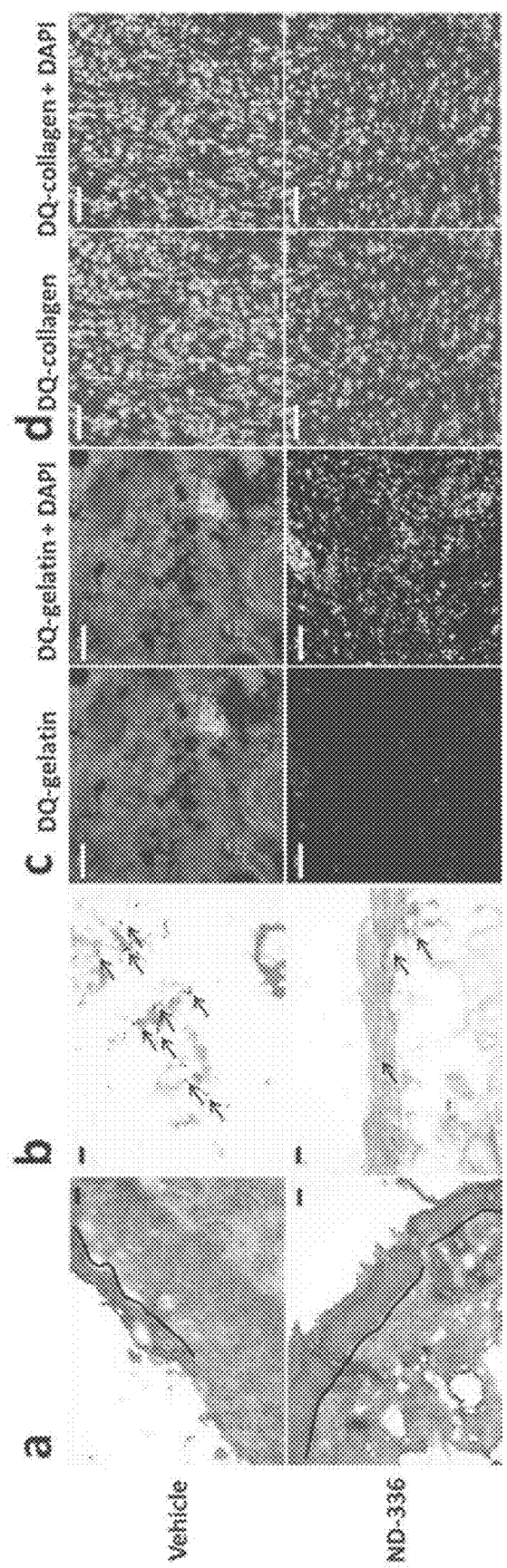
Fig. 4A-D

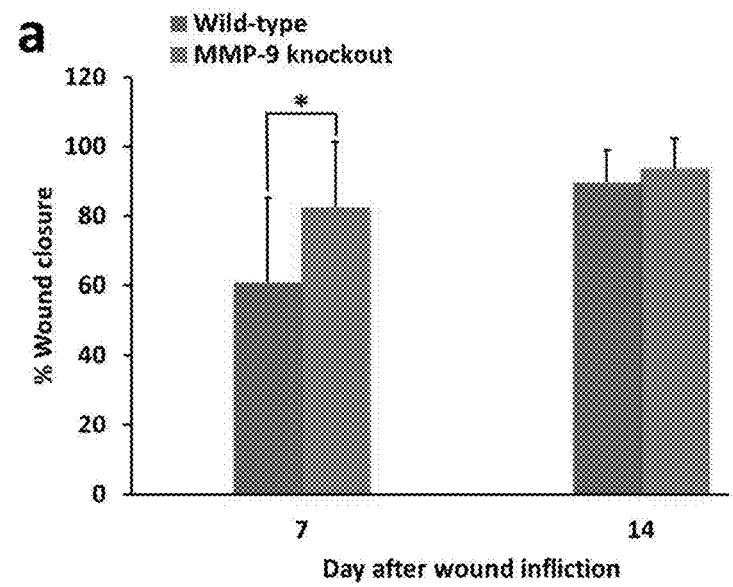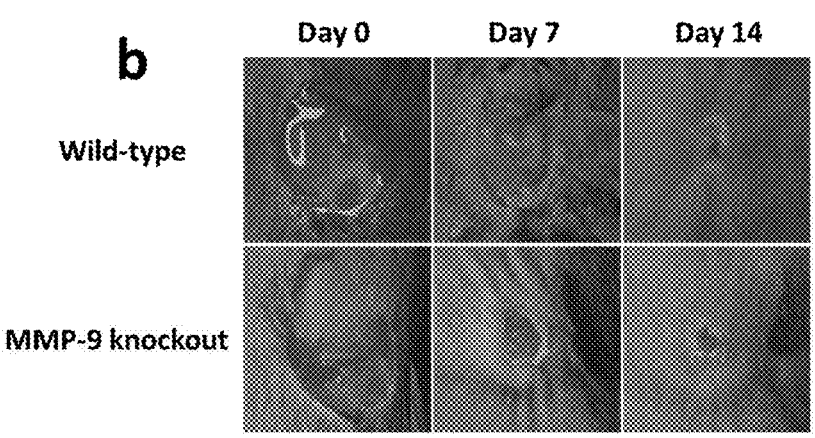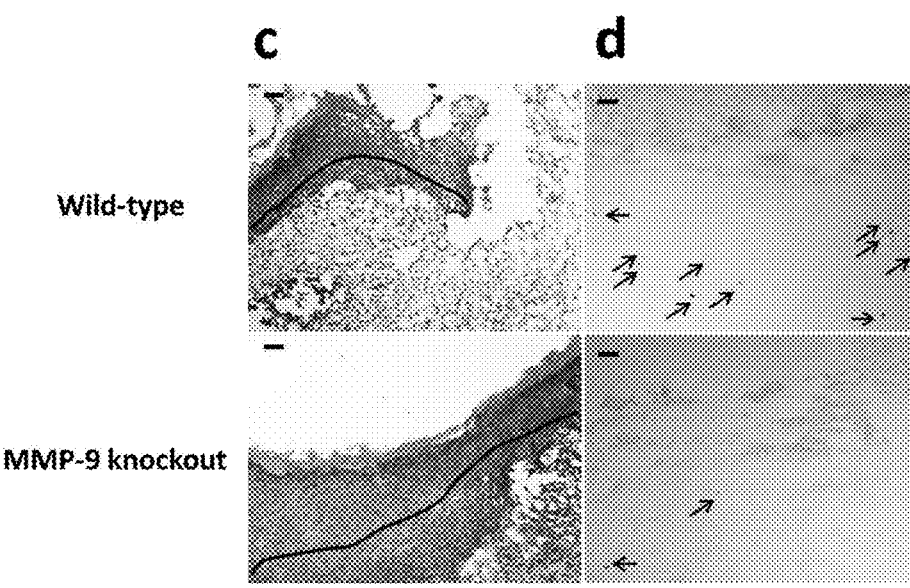
*Fig. 5A-D*

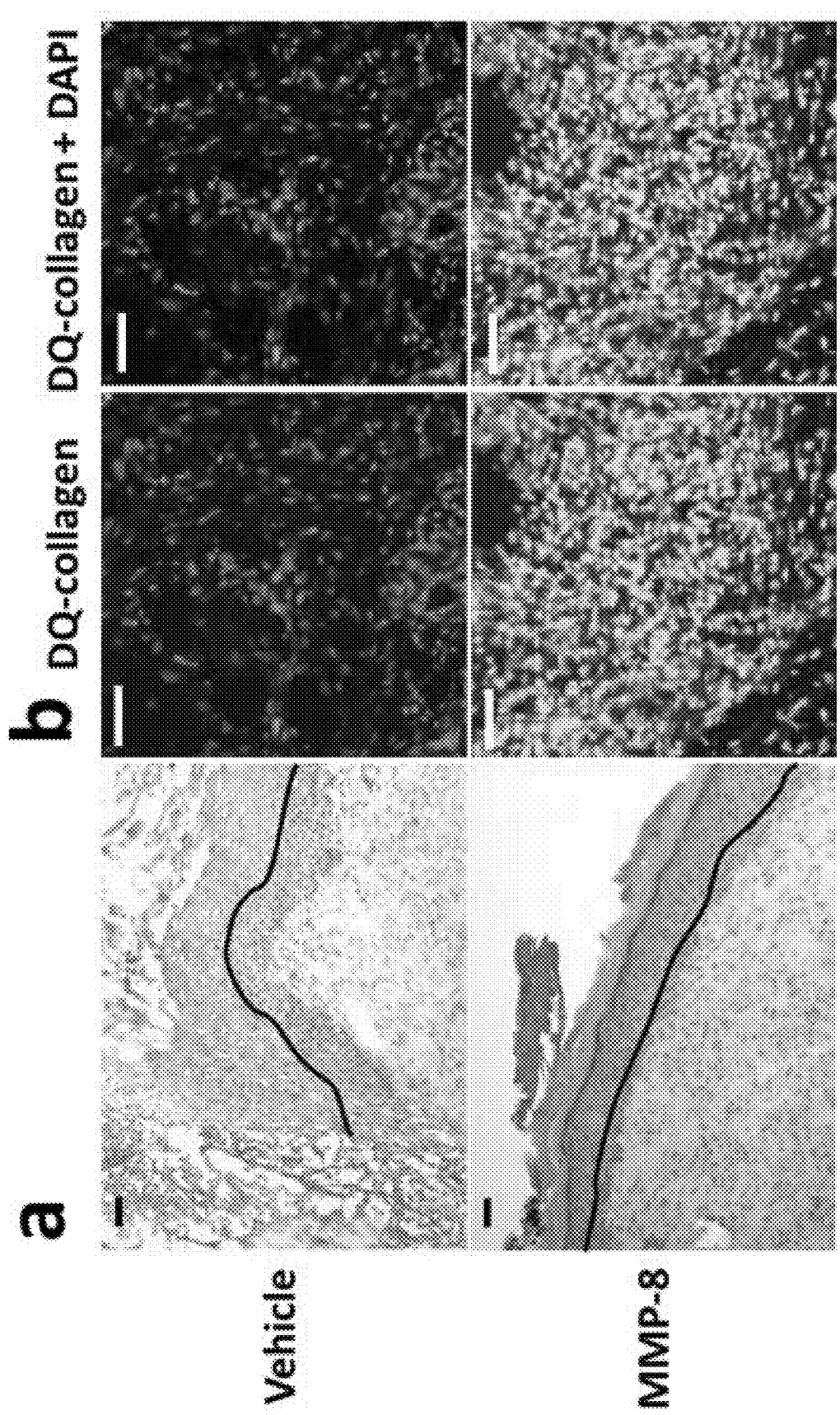
Fig. 6A-B

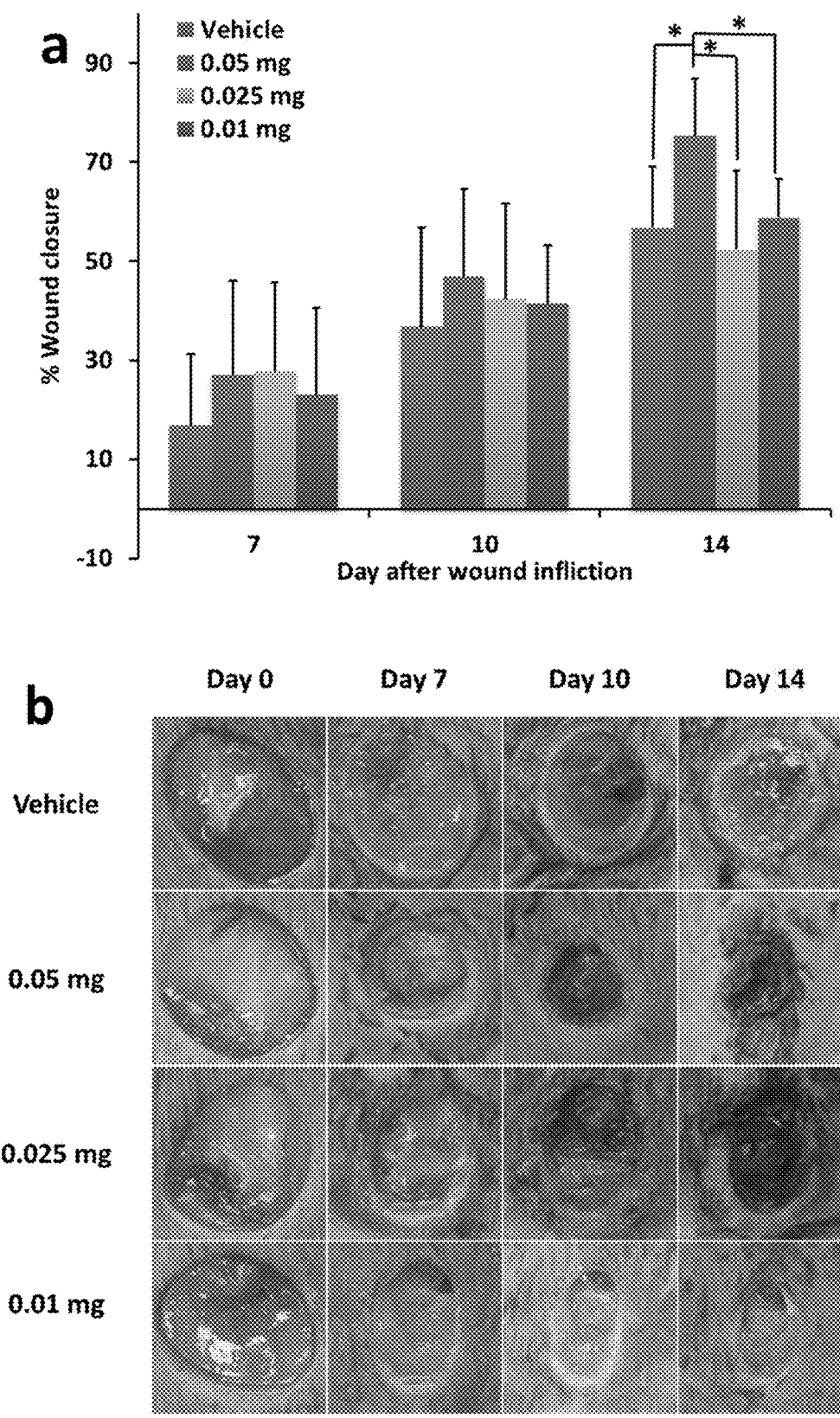
Fig. 7A-B

ACCELERATION OF DIABETIC WOUND HEALING

RELATED APPLICATIONS

This application is a National Stage entry under 35 U.S.C. § 371 of International Patent Application No. PCT/US2015/051252, filed Sep. 21, 2015, which claims priority under 35 U.S.C. § 119(e) to U.S. Provisional Patent Application Nos. 62/052,921, filed Sep. 19, 2014, and 62/128,871, filed Mar. 5, 2015, which applications are incorporated by reference.

BACKGROUND OF THE INVENTION

Diabetes affects 340 million people in the world, including 29.1 million individuals in the United States. A complication in diabetic patients is the inability of wounds to heal, which resulted in 73,000 lower-limb amputations in the United States in 2010. The standard treatment for diabetic foot ulcers includes debridement of the wound, treatment of infection with antibiotics, and reducing or eliminating weight pressure from the lower extremities. There is currently no pharmacological therapeutic available that accelerates wound healing without significant adverse effects.

In diabetic patients, high blood sugar triggers prolonged chronic inflammation, with concomitant elevated levels of matrix metalloproteinases (MMPs). The detrimental effect of MMPs in the diseased tissue has been attributed to rapid turnover of potential growth factors, receptors, and the newly formed extracellular matrix, which are essential for wound healing. Hence, wound healing is impaired and delayed in diabetic patients. However, this process is not well understood and the actual instigator MMPs is not known.

MMPs are a family of zinc-dependent endopeptidases that are capable of degrading extracellular matrix components and are involved in tissue remodeling and restructuring. MMPs are expressed as zymogens or pro-MMPs. Activation by proteolytic removal of the N-terminal pro-domain is required for their catalytic functions. Active forms of MMPs are highly regulated by binding of tissue inhibitors of metalloproteinases (TIMPs). MMPs are presumed to play various roles in regulating inflammatory and repair processes, as well as in wound healing.

In view of the inherent problems associated with chronic wounds and wound healing, there is a need for therapeutic compositions that are effective for the treatment of such wounds. There is also a need for selective therapies that are effective to enhance and accelerate the healing process, particularly in diabetic patients.

SUMMARY

Chronic wounds in diabetic patients are a devastating complication of diabetes that can lead to amputations or even death. Our work shows that matrix metalloproteinase (MMP)-9 contributes to delayed or impaired wound healing and that MMP-8 is involved in repairing the wound. A combination of a selective inhibitor of MMP-9 (a small molecule) and exogenously applied active recombinant MMP-8 (an enzyme) accelerates diabetic wound healing to provide a first-in-class therapy for the healing of diabetic wounds. The invention therefore provides compositions and methods for the acceleration of diabetic wound healing, for example, using a novel protease-anti-protease combination therapy, as described herein.

The inventors identified active MMP-8 in wounds of non-diabetic and diabetic mice, and found that MMP-9 was upregulated only in diabetic wounds. Treatment of wounds with a selective MMP-8 inhibitor delayed wound healing in diabetic animals. Selective inhibition of MMP-9 or ablation of the MMP-9 gene led to acceleration of wound healing in diabetic mice. Treatment of wounds with the enzyme MMP-8 accelerated wound healing in both diabetic and non-diabetic animals. These results demonstrate that MMP-8 plays a beneficial role in wound healing and that MMP-9 makes wounds refractory to healing. Thus, treatment of wounds with the enzyme MMP-8, with a combination of MMP-8 and an MMP-9 inhibitor, or with an MMP-9 inhibitor, accelerates wound healing.

Accordingly, the invention provides a therapeutic composition for treating a wound comprising an effective amount of the enzyme MMP-8 and an effective amount of a selective MMP-9 inhibitor. The selective MMP-9 inhibitor can be selective for MMP-9 over MMP-8, wherein the Ki value of the inhibitor for MMP-9 is at least 0.5 µM smaller than the Ki value of the inhibitor for MMP-8. Additionally, the selective MMP-9 inhibitor can be selective for MMP-9 over MMP-8, wherein the Ki value of the inhibitor for MMP-9 is at least 1 µM, at least 2 µM, or at least 5 µM smaller than the Ki of the inhibitor for MMP-8. In one embodiment, the MMP-9 inhibitor is:

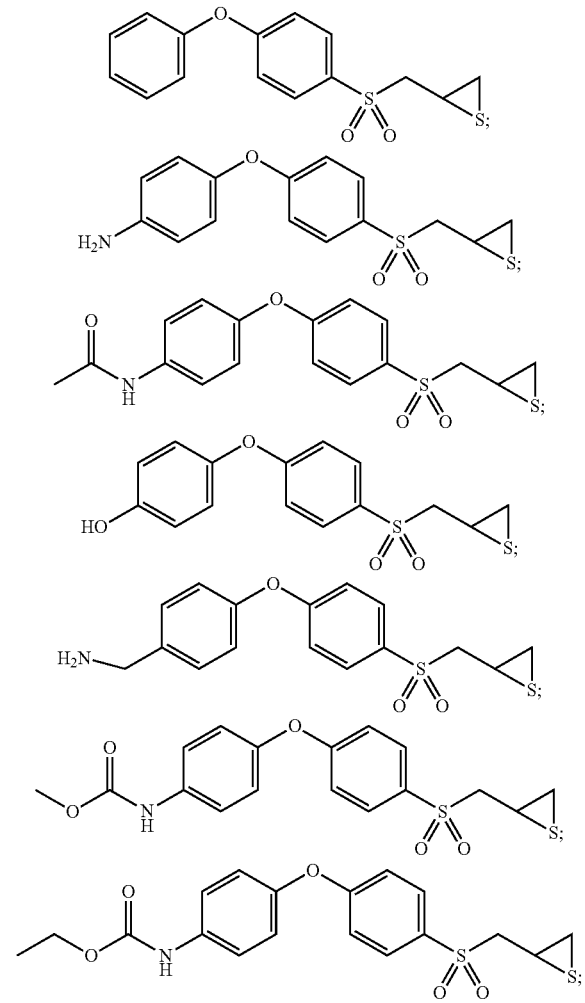

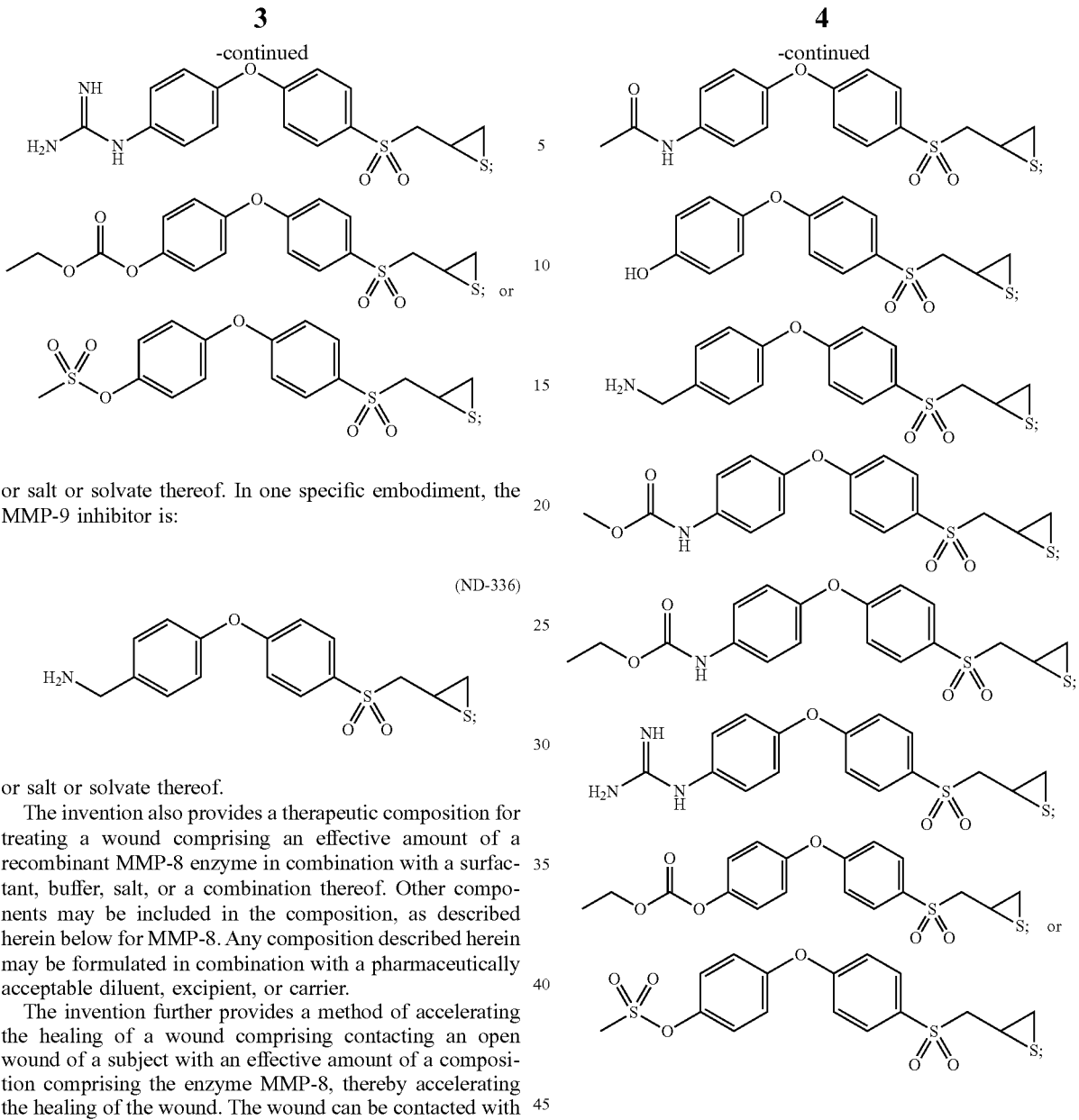

or salt or solvate thereof. In one specific embodiment, the MMP-9 inhibitor is:

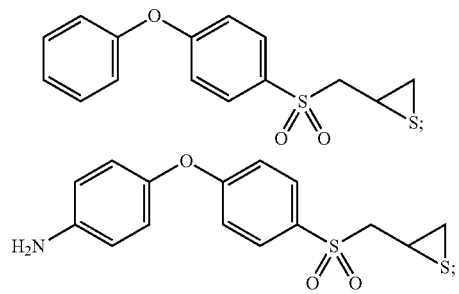
(ND-336)

or salt or solvate thereof.

The invention also provides a therapeutic composition for treating a wound comprising an effective amount of a recombinant MMP-8 enzyme in combination with a surfactant, buffer, salt, or a combination thereof. Other components may be included in the composition, as described herein below for MMP-8. Any composition described herein may be formulated in combination with a pharmaceutically acceptable diluent, excipient, or carrier.

The invention further provides a method of accelerating the healing of a wound comprising contacting an open wound of a subject with an effective amount of a composition comprising the enzyme MMP-8, thereby accelerating the healing of the wound. The wound can be contacted with at least about 0.5 μg of MMP-8 per 50 mm² of open wound per day. The method can further include administering to a subject having the open wound an effective amount of a selective MMP-9 inhibitor. The selective MMP-9 inhibitor can be selective for MMP-9 over MMP-8, wherein the Ki value of the inhibitor for MMP-9 is at least 0.5 μM smaller than the Ki value of the inhibitor for MMP-8.

In various embodiments, the MMP-9 inhibitor is:

or salt or solvate thereof. In further embodiments, the selective MMP-9 inhibitor is selective for MMP-9 over MMP-8, wherein the Ki value of the inhibitor for MMP-9 is at least 2 μM smaller than the Ki value of the inhibitor for MMP-8. In certain embodiments, the MMP-9 inhibitor is:

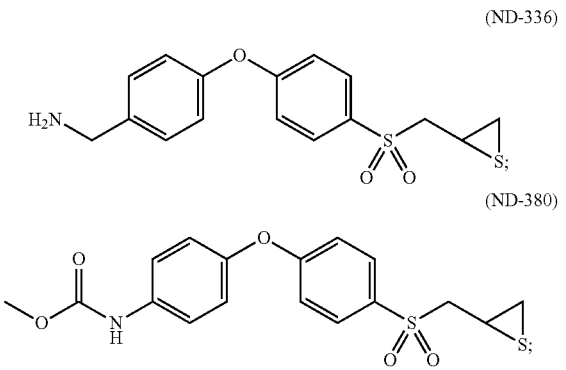
(ND-336)

(ND-380)

-continued

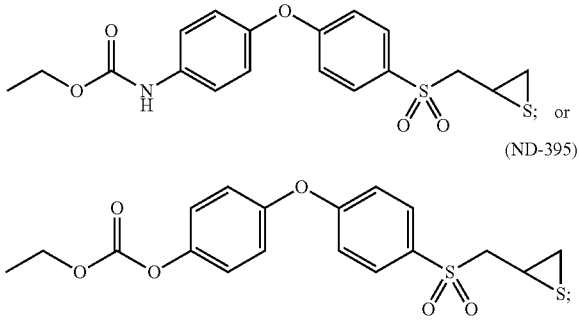

(ND-394)

(ND-395)

or salt or solvate thereof. In one particular embodiment, the MMP-9 inhibitor is ND-336.

In some embodiments, at least about 0.05 mg of the MMP-9 inhibitor is administered to the subject per 50 mm$^2$ of open wound per day. In various embodiments, the wound is a chronic wound. The subject can be a diabetic subject.

The invention additionally provides a method for decreasing inflammation and increasing angiogenesis in a diabetic wound comprising administering to a subject having a diabetic wound an effective amount of any one of the compositions described above or herein below.

The invention yet further provides a method for reducing the amount of apoptotic cells in a diabetic wound comprising administering to a subject having a diabetic wound an effective amount of any one of the compositions described above or herein below.

The invention also provides for the use of a composition comprising the enzyme MMP-8 for accelerating the healing of a wound. The wound can be a chronic wound, a diabetic wound, or a combination thereof.

The invention thus provides methods of accelerating the healing process of a wound. The wound can be internal, or the wound can be a wound of the integument, such as a skin wound. The methods can include administering to a mammal afflicted with a skin wound an effective amount of the enzyme MMP-8, or an effective amount of a combination of MMP-8 and an MMP-9 inhibitor; or a composition thereof.

The invention provides for the use of the compositions described herein for use in medical therapy. The medical therapy can include accelerating the healing of a wound, such as a wound of an animal, for example, a human. The invention also provides for the use of a composition as described herein for the manufacture of a medicament to treat wound conditions in animals. The medicament can include a pharmaceutically acceptable diluent, excipient, or carrier. The medicament can be administered to a subject topically, enterally, or parenterally.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2A-D. Effect of MMP-9 inhibition and exogenous MMP-8 on diabetic wound healing. Mice received a single 8 mm excisional wound on the dorsal thorax. Wounds were treated with vehicle, ND-336 (0.05 mg/wound/day), MMP-8 (1 μg/wound/day), or ND-336 (0.05 mg/wound/day) plus MMP-8 (1 μg/wound/day). (a) H&E staining for representative wounds on day 14. Re-epithelialization is indicated by the black line. Pictures are taken with 10× lens. Scale bars are 50 μm. (b) TUNEL images of representative wounds on day 14. Arrows point to representative TUNEL-positive cells (apoptotic cells). Pictures are taken with 10× lens. Scale bars are 50 μm. (c) In-situ zymography with gelatinase fluorogenic substrate DQ-gelatin (green on the left panels) and merged with nuclear DNA staining by DAPI (blue on the right panels). Pictures are taken with 40× lens. Scale bars are 50 μm. (d) In-situ zymography with collagenase fluorogenic substrate DQ-collagen (green on the left panels) and merged with nuclear DNA staining by DAPI (blue on the right panels). Pictures are taken with 40× lens. Scale bars are 50 μm.

FIG. 3A-F. MMP-9 inhibition and/or exogenous MMP-8 result in decreased inflammation and increased angiogenesis (line key: circle=vehicle; square=ND-336; triangle=MMP-8; inverted triangle=ND-336+MMP-8). (a) Concentrations of IL-6 as a function of time after wound infliction; * $p<0.05$, # $p<0.01$ indicate statistically significant differences in IL-6 between vehicle and the indicated group. (b) Area-under-the-curve (AUC) for IL-6 showed that IL-6 levels were significantly reduced upon treatment with ND-336, MMP-8, or combined ND-336 and MMP-8. (c) Concentrations of TGF-β1 as a function of time after wound infliction; * $p<0.05$, # $p<0.01$ indicate statistically significant differences in TGF-β1 between vehicle and the indicated group. (d) Area-under-the-curve (AUC) for TGF-β1 showed that TGF-β1 levels were significantly reduced upon treatment with ND-336, MMP-8, or combined ND-336 and MMP-8. (e) Concentrations of VEGF as a function of time after wound infliction; * $p<0.05$, # $p<0.01$ indicate statistically significant differences in VEGF between vehicle and the indicated group. (f) Area-under-the-curve (AUC) for VEGF showed that VEGF levels were significantly increased upon treatment with ND-336, MMP-8, or combined ND-336 and MMP-8.

FIG. 4A-D. Effect of MMP-9 inhibition on diabetic wound healing. A single 8 mm wound was made on the dorsal thorax. Wounds were treated with ND-336 (0.1 mg/wound/day or vehicle. (a) H&E staining on day 14. Re-epithelialization is indicated by the black line. Pictures are taken with 10× lens. Scale bars are 50 μm. (b) TUNEL images of wounds on day 14. Arrows point to representative TUNEL-positive cells (apoptotic cells). Pictures are taken with 10× lens. Scale bars are 50 μm. (c) In-situ zymography with gelatinase fluorogenic substrate DQ-gelatin (green on the left panels), and merged with nuclear DNA staining by DAPI (blue on the right panels). Pictures are taken with 40× lens. Scale bars are 50 μm. (d) zymography with collagenase fluorogenic substrate DQ-collagen (green on the left panels) and merged with nuclear DNA staining by DAPI (blue on the right panels). Pictures are taken with 40× lens. Scale bars are 50 μm.

FIG. 5A-D. Effect of MMP-9 gene ablation on diabetic wound healing. Diabetes was induced in wild-type and MMP-9 knockout mice by treatment with streptozotocin (150 mg/kg ip) and confirmed by fasting blood glucose of >300 mg/dL. Excisional 8 mm wounds were inflicted two weeks later. (a) Wound healing in wild-type and MMP-9 knockout streptozotocin-induced diabetic mice. Mean±SD; n=13 and 7 per group on days 7 and 14, respectively; * p<0.05 indicates statistically significant differences in wound healing between the two indicated groups. (b) Representative wound images (all to the same scale) on days 0, 7, and 14. (c) H&E staining for representative wounds in wild-type and MMP-9 knockout streptozotocin-induced diabetic mice. Re-epithelialization is indicated by the black line. Pictures are taken with 10× lens. Scale bars are 50 μm. (d) TUNEL images of representative wounds on day 7. Arrows point to representative TUNEL-positive cells (apoptotic cells). Pictures are taken with 10× lens. Scale bars are 50 μm.

FIG. 6A-B. Topical treatment with exogenously added MMP-8 accelerates wound healing in db/db mice. A single 8-mm punch biopsy lesion on the dorsal thorax was given to mice. Wounds were treated with MMP-8 (1 μg/wound/day) or vehicle (saline). (a) H&E staining for representative wounds treated with vehicle or MMP-8. Re-epithelialization is indicated by the black line. Pictures are taken with 10× lens. Scale bars are 50 μm. (b) In-situ zymography with collagenase fluorogenic substrate DQ-collagen (green on the left panels), and merged with nuclear DNA staining by DAPI (blue on the right panels). Pictures are taken with 40× lens. Scale bars are 50 μm.

FIG. 7A-B. Dose response of ND-336 in diabetic wound healing. (a) Wound healing in db/db mice treated with ND-336 at 0.05, 0.025, and 0.01 mg/wound/day. Mean±SD; n=7/group on days 7, 10, and 14; * p<0.05 indicates statistically significant differences in wound healing. (b) Representative wound images (all to the same scale) on days 0, 7, 10, and 14.

DETAILED DESCRIPTION

Figure 1A:
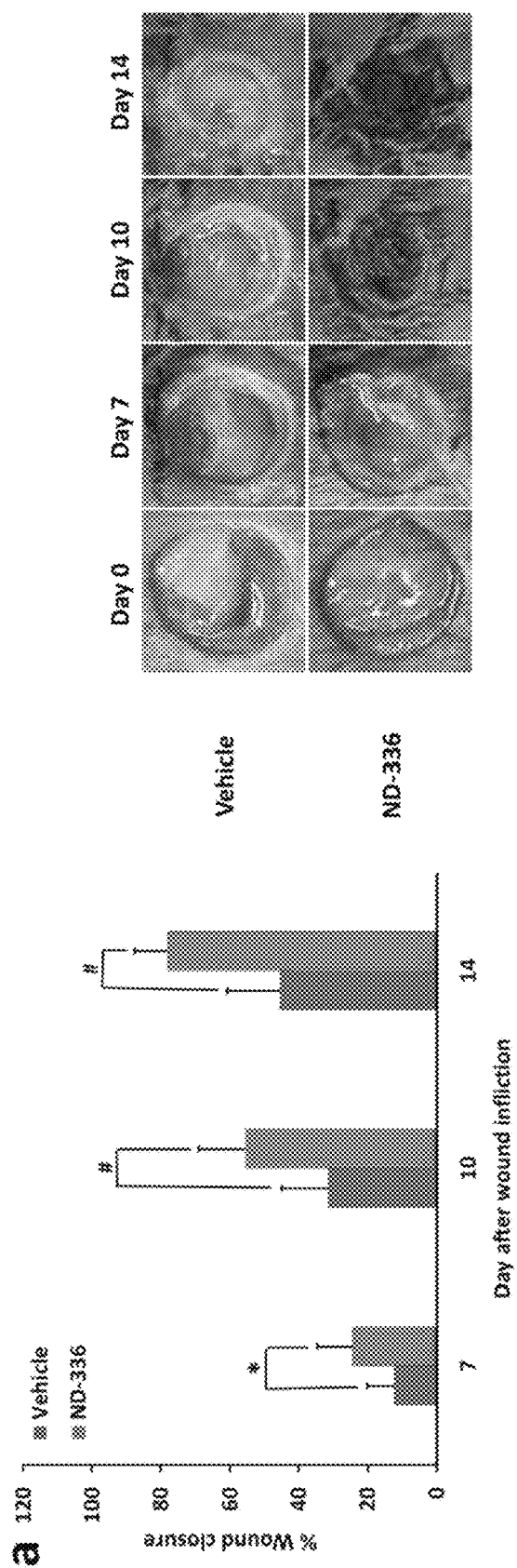
FIG. 1A-C. Effect of MMP-9 inhibition, topical treatment with exogenously added MMP-8, and combined MMP-9 inhibition and exogenous MMP-8 on diabetic wound healing. A single 8 mm wound was made on the dorsal thorax of db/db mice. * $p<0.05$, # $p<0.01$ indicate statistically significant differences in wound closure between the indicated groups. (a) Wound healing after treatment with ND-336 (0.1 mg/wound/day). Mean±SD; n=8/group on days 7, 10, and 14; (b) Wound healing after exogenously added MMP-8 (1 μg/wound/day). Mean±SD; n=11, 6, and 5 on days 7, 10, and 14, respectively, for the vehicle group; n=10, 5, and 5 on days 7, 10, and 14, respectively, for the MMP-8 group; (c) Wound healing after treatment with combined ND-336 (0.05 mg/wound/day) and MMP-8 (1 μg/wound/day). Mean±SD; n=5, 6, 4 and 4 for vehicle, ND-336, MMP-8 and ND-336+MMP-8 groups, respectively.

The inventors have identified and quantified active MMP-8 and MMP-9 in a mouse model of diabetic wound healing by the use of a novel inhibitor-tethered resin that binds exclusively to active MMPs, in conjunction with proteomics analyses (Gooyit et al. (2014) *ACS Chem Biol* 9:505-510). Because MMP-9 was observed upregulated only in diabetic wounds and MMP-8 was found in both diabetic and non-diabetic wounds, we hypothesized that MMP-8 was beneficial and that MMP-9 was detrimental in diabetic wound healing. We now report that the use of either an MMP-9 inhibitor or application of the active recombinant MMP-8 accelerates wound healing in diabetic mice. Particularly effective is a novel and highly selective MMP-9 inhibitor of our design (ND-336, compound 1).

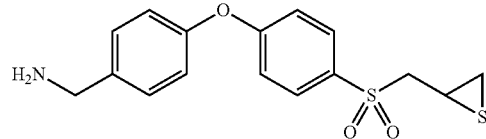

ND-336 (1)

We further confirmed the detrimental effect of MMP-9 on diabetic wound healing by the use of MMP-9-knockout mice. Finally, we document that the combination of selective small molecule MMP-9 inhibitors plus the active recombinant MMP-8 enzyme accelerates wound healing even further in diabetic subjects. These therapies provide a first-in-class pharmacological treatment for diabetic wound healing, which therapies hold great promise for recourse in this devastating disease.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

For medical treatment, an "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) inhibiting a disease, pathologic or medical condition or arresting its development; (ii) relieving the disease, pathologic or medical condition; and/or (iii) diminishing symptoms associated with the disease, pathologic or medical condition. Thus, the terms "treat", "treatment", and "treating" can include lowering, lessening, stopping or reversing the progression or severity of the condition or symptoms being treated. As such, the term "treatment" can include medical and/or therapeutic administration, as appropriate.

The terms "inhibit", "inhibiting", and "inhibition" refer to the slowing, halting, or reversing the growth or progression of a disease, infection, condition, activity, or group of cells. The inhibition can be greater than about 20%, 40%, 60%, 80%, 90%, 95%, or 99%, for example, compared to the growth or progression or activity that occurs in the absence of the treatment or contacting.

The terms "increase", "enhance", and "accelerate" with respect to wound healing and wound management refer to the faster re-epithelialization of a wound, optionally in combination with decreased inflammation and/or increased angiogenesis, in a wound, for example, a diabetic wound, and/or reduced amount of apoptotic cells in a diabetic wound. The increasing, enhancing, or accelerating of wound healing can be about 5% greater (with respect to re-epithelialization of the wound), up to about 2-fold or 3-fold greater than the healing occurs in the absence of the treatment or contacting with the compound or composition described herein. In some embodiments, the increasing, enhancing, or accelerating of wound healing can be greater than about 5%, greater than about 10%, greater than about 20%, greater than about 25%, greater than about 30%, greater than about 40%, or greater than about 50%, up to about 3-fold or 4-fold, for example, compared to the wound healing (e.g., re-epithelialization, decrease in inflammatory markers, increase in angiogenesis, or reduction of apoptotic cells) that occurs in the absence of the treatment or contacting. The enhanced healing occurs without increased rates of malignancy in the subject, such as the increased malignancy associated with the use of becaplermin.

The compositions and methods described herein can be used for aiding wound management. The term "wound management" refers to therapeutic methods that induce and/or promote repair of a wound including, but not limited to, arresting tissue damage such as necrotization, promoting tissue growth and repair, reduction or elimination of an established microbial infection of the wound and prevention of new or additional microbial infection or colonization. The term can further include reducing or eliminating the sensation of pain attributable to a wound.

A "wound" refers to an injury to the body, including but not limited to an injury from trauma, violence, accident, or surgery. A wound may occur due to laceration or breaking of a membrane (such as the skin) and usually damage to underlying tissues. A wound may occur in a topical location or internally. Chronic wounds may be caused by diseases, including but not limited to diabetes; diseases of internal organs, including but not limited to diseases of the liver, kidneys or lungs; cancer; or any other condition that slows the healing process.

Natural healing occurs in clearly defined stages. Skin wounds of acute nature may heal in 1-3 weeks in a biological process that restores the integrity and function of the skin and the underlying tissue. Such wounds may be the result of a scrape, abrasion, cut, graze, incision, tear, or bruise to the skin. If a wound does not heal in 4-12 weeks, it may be considered chronic. In the case of chronic wounds, the wound may be attenuated at one of the stages of healing or fail to progress through the normal stages of healing. A chronic wound may have been present for a brief period of time, such as a month, or it may have been present for several years. The compositions and methods described herein can initiate and enhance the healing of a chronic wound, such as a chronic skin wound.

The phrase "chronic skin wound" includes, but is not limited to, skin ulcers, bed sores, pressure sores, diabetic ulcers and sores, and other skin disorders. Chronic skin wounds can be any size, shape or depth, and may appear discolored as compared to normal, healthy skin pigment. Chronic skin wounds can bleed, swell, seep purulent discharge or other fluid, cause pain or cause movement of the affected area to be difficult or painful. Chronic skin wounds can become infected, producing elevated body temperatures, as well as pus or discharge that is milky, yellow, green, or brown in color. The discharge can be odorless or have a pungent odor. If infected, chronic skin wounds may be red, tender, or warm to the touch.

Chronic skin wounds can be caused by diabetes, poor blood supply, low blood oxygen, by conditions where blood flow is decreased due to low blood pressure, or by conditions characterized by occluded, blocked or narrowed blood vessels. A low oxygen supply can be caused by certain blood, heart, and lung diseases, and/or by smoking cigarettes. Chronic skin wounds can also be the result of repeated trauma to the skin, such as swelling or increased pressure in the tissues, or constant pressure on the wound area. Chronic skin wounds can also be caused by a weakened or compromised immune system. A weakened or compromised immune system can be caused by increasing age, radiation, poor nutrition, and/or medications, such as anti-cancer medicines or steroids. Chronic skin wounds can also be cause by bacterial, viral or fungal infections, or the presence of foreign objects.

Therapeutic compositions for use in methods of wound healing and wound management can include one or more surfactants. The surfactant can useful in cleaning a wound or contributing to bactericidal activity of the administered compositions. Suitable surfactants include, but are not limited to, phospholipids such as lecithin, including soy lecithin, and various detergents. In compositions for application to a wound or skin surface, when a surfactant in included in the composition, the surfactant selected can be mild and not lead to extensive irritation or promote further tissue damage to the patient. The surfactant can be a non-natural (e.g., synthetic) surfactant.

A surfactant can be present in the composition at a concentration of about 0.1 wt % to about 25 wt %, about 1 wt % to about 20 wt %, about 2 wt % to about 20 wt %, or about 5 wt % to about 10 wt %. Suitable nonionic surfactants that can be used in the therapeutic compositions described herein can include, for example, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronics); fatty acid alkylolamides (fatty acid amide polyethylene glycols); alkyl polyglycosides, N-alkyl-N-alkoxypolyhydroxy fatty acid amides, in particular N-methyl-fatty acid glucamide; sucrose esters; sorbitol esters, and esters of sorbitol polyglycol ethers. In one embodiment, the surfactant is a polypropylene glycol ethoxylate such as the poloxymer Pluronic F-127 (Poloxamer 407). In other embodiments, the surfactant(s) can include lecithin, with or without the addition of Pluronic F-127 in about 2 wt % to about 20 wt %, for increasing the viscosity or gelling of the compositions.

Acceleration of Wound Healing.

Non-healing chronic wounds are major complications of diabetes, which result in >70,000 annual lower-limb amputations in the United States alone. The basis for why the diabetic wound is recalcitrant to healing is not fully understood and there are no therapeutic agents that accelerate or facilitate its repair. We have identified two active forms of matrix metalloproteinases (MMPs), MMP-8 and MMP-9, in the wounds of diabetic mice. We thought that MMP-8 might play a role in the body's response to wound healing and that MMP-9 was the pathological consequence of the disease with detrimental effects.

We demonstrate herein that the use of inhibitors of MMP-9, including a novel highly selective inhibitor of MMP-9 (compound ND-336), accelerate diabetic wound healing by lowering inflammation, and by enhancing angiogenesis and re-epithelialization of the wound, hence reversing the pathological condition. The detrimental role of MMP-9 to the pathology of diabetic wounds was further confirmed by the study of diabetic MMP-9-knockout mice, which exhibited wounds more prone to healing. Furthermore, topical administration of active recombinant MMP-8 also accelerated diabetic wound healing as a consequence of complete re-epithelialization, diminished inflammation, and enhanced angiogenesis. The combined topical application of an MMP-9 inhibitor (a small molecule) and the active recombinant MMP-8 (an enzyme) enhanced healing even more, a strategy that can be a first-in-class therapeutic in the healing of diabetic wounds.

Synthesis and MMP Inhibition Profile of ND-336.

There are 23 MMPs in humans and their catalytic domains are very similar in structure, thus, the design of inhibitors that are selective for a particular MMP is extremely challenging. In fact, most inhibitors of MMPs are zinc chelators, which broadly inhibit many or all MMPs, as well as the related ADAMs (a disintegrin and metalloproteinase). Over the past several years we have produced a library of thiirane inhibitors for MMPs (Gooyit et al. (2011) Selective water-soluble gelatinase inhibitor prodrugs. *J Med Chem* 54(19):6676-6690; Lee et al. (2012) Structure-Activity Relationship for Thiirane-Based Gelatinase Inhibitors. *ACS Med Chem Lett* 3(6):490-495; Testero S A, et al. (2010) Sulfonate-containing thiiranes as selective gelatinase inhibitors. *Med Chem Lett*.), which allowed for identification of specific inhibitors for selective inhibition of enzymes involved in various MMP-mediated diseases. The thiiranes undergo a reaction catalyzed by the target MMP, resulting in opening of the thiirane ring and generation of the thiolate, which is a tight-binding inhibitor (Forbes et al. (2009) Active site ring-opening of a thiirane moiety and picomolar inhibition of gelatinases. *Chem Biol Drug Des* 74(6):527-534). When we identified active MMP-8 and MMP-9 in the diabetic wounds, and hypothesized that MMP-9 played a detrimental role in the disease, the central criterion for selectivity of a suitable inhibitor became its ability to differentiate between MMP-8 and MMP-9, as the latter had to be inhibited in the presence of active MMP-8. We now report on the discovery of compound 1, which meets the requirements for potent inhibition of MMP-9 and lack thereof for MMP-8.

The binding constants for ND-336 with seven representative MMPs and two related ADAMs are given in Table 1. ND-336 inhibits MMP-2, MMP-9 and MMP-14 in a slow-binding mechanism, with inhibition constant ($K_i$) values of 85±1 nM, 150±10 nM, and 120±10 nM, respectively.

TABLE 1

Inhibition profile of ND-336

| Enzyme | Inhibition type | $k_{on}$ ($s^{-1}M^{-1}$) | $k_{off}$ ($10^3 s^{-1}$) | Ki |
|---|---|---|---|---|
| MMP-1[b] | | | | 4% inhibition @ 100 µM |
| MMP-2 | slow-binding | 8380 ± 110 | 0.712 ± 0.006 | 85 ± 1 nM[a] |
| MMP-3[b] | | | | 23% inhibition @ 100 µM |
| MMP-7 | | | | 1% inhibition @ 100 µM |
| MMP-8[b] | linear non-competitive | | | 7700 ± 100 nM |
| MMP-9[b] | slow-binding | 2360 ± 100 | 0.352 ± 0.033 | 150 ± 10 nM[a] |
| MMP-14[b] | slow-binding | 10800 ± 400 | 1.33 ± 0.03 | 120 ± 10 nM[a] |
| ADAM9 | | | | 31% inhibition @ 100 µM |
| ADAM10 | | | | 14% inhibition @ 100 µM |

[a]Calculated from the ratio of $k_{off}/k_{on}$.
[b]Catalytic domains.

As MMP-2 and MMP-14 are absent in the diabetic wound, the inhibitor targets essentially MMP-9 in this microenvironment. The residence times (the time the drug remains bound to the target; calculated as $1/k_{off}$) of ND-336 are: 23.4±0.2 min for MMP-2, 47.4±4.4 min for MMP-9, and 12.6±0.3 min for MMP-14. For comparison, the residence times of the endogenous protein inhibitor TIMPs are shorter: 6.9 min for MMP-2-TIMP1, 10.4 min for MMP-2-TIMP2, 7.9 min for MMP-9-TIMP1, and 6.7 min for MMP-9-TIMP2. That is, ND-336 is better at inhibiting MMP-2 and MMP-9 than TIMPs that have evolved for this purpose. ND-336 exhibits marginal to no inhibition of MMP-1, MMP-3, MMP-7, ADAMS and ADAM10, and it poorly inhibits MMP-8 in a linear noncompetitive manner ($K_i$=7700±100 nM). Combined with the 50-fold lower $K_i$ for MMP-9, the exceptional residence time contributes substantially to selectivity. The residence time is an important contributor for effective inhibition of MMP-9. This is in contrast to the linear noncompetitive inhibition of MMP-8 by ND-336, with a very short residence time and poorer dissociation constant.

Inhibition of MMP-9 with ND-336 in Diabetic Wound Healing.

ND-336 was evaluated in a mouse model of diabetic wound healing. Excisional wounds were made on the dorsal thorax of diabetic mice and the wounds were topically treated with either vehicle or ND-336. Wounds treated with ND-336 healed about 2-fold faster, than those given vehicle (FIG. 1a). As human wounds heal by re-epithelialization, we evaluated the wounds with hematoxylin-eosin (H&E) staining for visualization of the epithelium. Treatment with ND-336 resulted in almost complete re-epithelialization compared to partial re-epithelialization in the vehicle-treated group (FIG. 4a). As MMP-9 activity is associated with induction of apoptosis, we evaluated the wounds by the terminal deoxynucleotidyl transferase dUTP nick-end labeling (TUNEL), which detects DNA fragmentation resulting from apoptotic cells. As shown in FIG. 4b, numerous apoptotic cells were found in the vehicle group, while apoptosis was significantly decreased in the ND-336-treated group.

In-situ zymography detects MMP activity in vivo using the fluorogenic substrates: DQ-gelatin for gelatinase (MMP-2 and MMP-9) activity and DQ-collagen for collagenase (MMP-1, MMP-8, and MMP-13) activity. Since only active MMP-8 and MMP-9 were identified by our proteomics analyses in diabetic wounds, the gelatinase activity observed by in-situ zymography corresponds to MMP-9 activity and the collagenase activity is reflective of MMP-8 activity. Treatment with ND-336 significantly decreased MMP-9 activity (FIG. 4c left), while MMP-8 activity was not affected (FIG. 4d left), as expected from the kinetic profile of ND-336 (Table 1). Merged images stained with DAPI (blue) indicated comparable number of nuclei in the wound tissues treated with vehicle and ND-336 (FIGS. 4c right and 4d right).

Ablation of MMP-9 in Diabetic Wound Healing.

We induced diabetes in MMP-9 knockout mice to confirm the detrimental role of MMP-9 in diabetic wound healing. We administered streptozotocin, which destroys insulin-producing beta cells in the pancreas by necrosis and used wild-type mice treated with streptozotocin as the control group. As seen in FIG. 5, the wounds of streptozotocin-treated MMP-9 knockout mice healed faster than those of streptozotocin-treated wild-type and resulted in complete re-epithelialization, as well as diminished apoptosis. This study confirmed that MMP-9 is involved in the pathology of diabetic wounds. Since enhanced expression of MMP-8 occurs in MMP-9 knockout mice, the acceleration of wound healing that we observe in diabetic MMP-9 knockout mice could be explained by the upregulation of MMP-8 and the absence of MMP-9. Our findings in MMP-9 knockout diabetic mice differ from those of Kyriakides et al., who suggested that MMP-9 is required for normal progression of wound closure since MMP-9 gene ablation in non-diabetic mice led to delayed wound healing due to compromised re-epithelialization, attenuated keratinocyte wound migration, and reduced clearance of fibrin clots (Kyriakides et al. (2009) *Matrix biology: J. Internat. Soc. for Matrix Biology* 28(2):65-73). However, inflammation and angiogenesis in wounds of non-diabetic MMP-9 knockout mice were similar to those in control mice. Others have found that skin inflammation is alleviated in MMP-9 knockout mice (Purwar et al. (2008) *J Invest Dermatol* 128(1):59-66) and that inhibition of MMP-9 with leptomycin B suppressed inflammation in ultraviolet B irradiated murine skin (Kobayashi & Shinkai (2005) *J Invest Dermatol* 124(2):331-337), consistent with our findings.

Effect of MMP-8 in Diabetic Wound Healing.

Figure 1B:
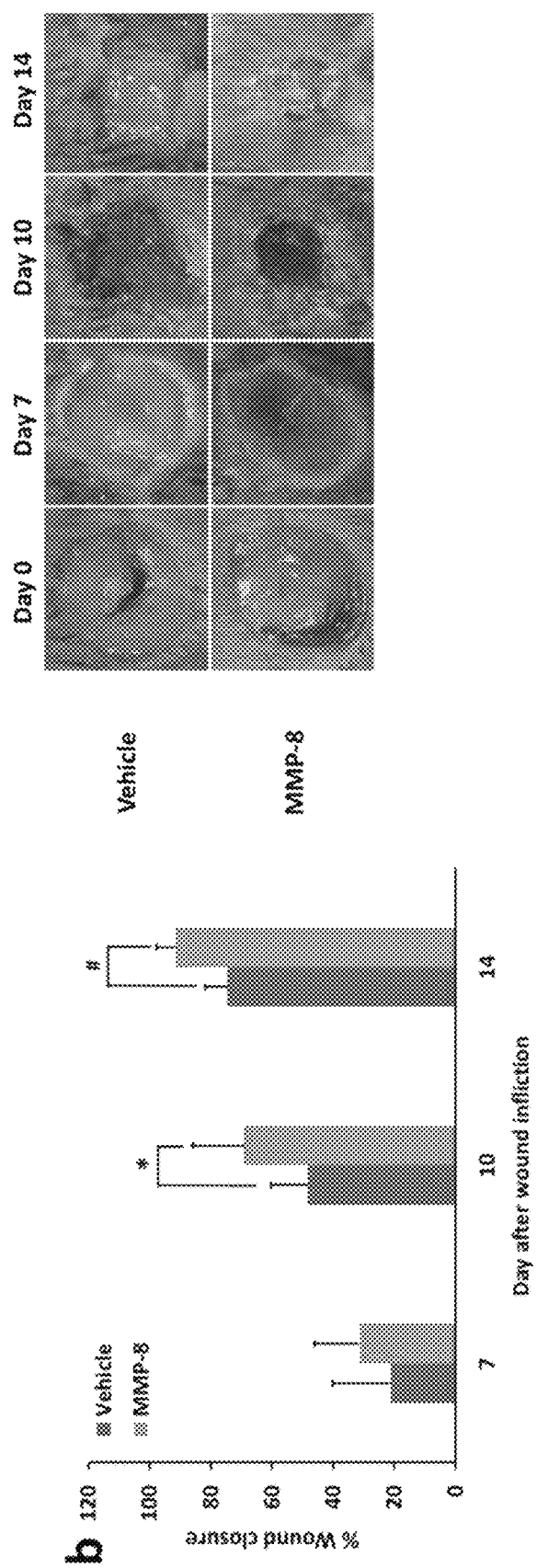

To test the hypothesis that MMP-8 contributes to the repair in diabetic wound healing, we evaluated the effect of topical application of the protease MMP-8 to wounds of diabetic mice. We cloned the gene, expressed, and purified active murine recombinant MMP-8 (see Example 2 below). The active recombinant MMP-8 was applied topically to the wounds at 10-fold the level found in the wounds (Gooyit et al. (2014) *ACS Chem Biol* 9:505-510). MMP-8 accelerated wound healing at this level in diabetic mice, with statistical differences observed on days 10 and 14 (FIG. 1b) and resulted in complete re-epithelialization (FIG. 6a). Increased MMP-8 activity in the MMP-8-treated diabetic mice was confirmed by in-situ zymography (FIG. 6b). This study indicates that MMP-8 plays a beneficial repair role in diabetic wound healing. Our findings are in agreement with those of Gutierrez-Gernandez et al. who found that non-diabetic mice deficient in MMP-8 have delayed wound healing ((2007) *FASEB J* 21(10):2580-2591). Interestingly, MMP-8 knockout mice have significantly increased levels of MMP-9, due to compensatory expression, which contributes to delayed wound healing.

Effect of the Combination of MMP-9 Inhibitor and Exogenously Added Active Recombinant MMP-8.

Figure 1C:
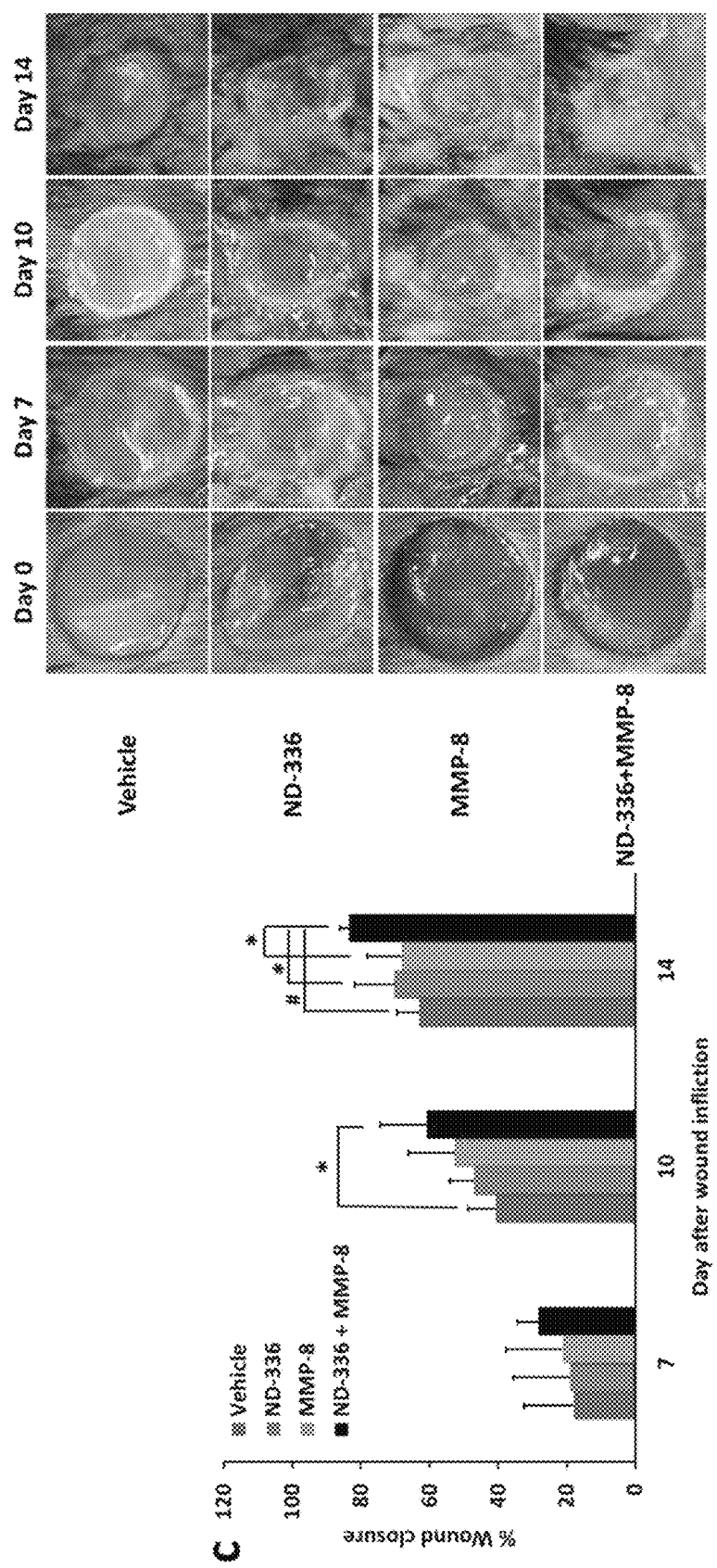

As either inhibition of MMP-9 by a small molecule MMP-9 inhibitor (e.g., ND-336) or topically applied exogenously added active recombinant MMP-8 alone accelerated wound healing, we investigated the effect of the combination therapy. We first determined that 0.05 mg/kg/day of ND-336 applied to diabetic wounds was the lowest dose that accelerated wound healing (FIG. 7). As can be observed in FIG. 1c, the combined treatment not only showed significant acceleration of wound healing compared to the vehicle group on both days 10 and 14, but it also showed significant faster healing on day 14 than when a single agent was used in the treatment.

Histological assessment of the wound revealed that the combination of the MMP-9 inhibitor and MMP-8 resulted in complete re-epithelialization compared to either of the two agents by itself or the vehicle (FIG. 2a) and substantial reduction in apoptotic cells relative to the other three groups (FIG. 2b) (a 75% reduction). In-situ zymography with DQ-gelatin showed inhibition of MMP-9 in the ND-336-treated group and in the combination of ND-336- and MMP-8-treated groups (FIG. 2c, left). With DQ-collagen, in-situ zymography indicated the presence of MMP-8 in the vehicle- and ND-336-treated groups, while significantly increased MMP-8 activity was found in the MMP-8 group and in the group for the combination of ND-336 and MMP-8 (FIG. 2d left).

MMP-9-Inhibition and Exogenously Added MMP-8 Decrease Inflammation and Enhance Angiogenesis.

Inflammation is necessary for normal wound healing. However, increased or prolonged inflammation has been shown to delay wound healing in non-diabetic mice. Interleukin-6 (IL-6) plays a crucial role in the inflammatory response in wound repair and it is a proinflammatory cytokine. IL-6 deficient mice display impaired wound healing, which is reversed with administration of IL-6. Delayed wound healing in IL-6 knockout mice was accompanied by attenuated leukocyte infiltration, re-epithelialization, angiogenesis, and collagen accumulation. Transforming growth factor-β1 (TGF-β1) is a cytokine that elicits recruitment of inflammatory cells during wound healing. TGF-β1 is unregulated during wound healing, indicating that it regulates wound repair. Immunodeficient TGF-β1 knockout mice show delayed wound healing, with accompanying delays in the inflammatory, proliferation, and maturation phases of wound healing. TGF-β induces pro-MMP-9 in human skin and TGF-β1 stimulates the production of MMP-9 in human corneal epithelial cells and in human keratinocytes. Enhanced TGF-β1 signaling accelerates re-epithelialization.

These findings indicate that IL-6 and TGF-β1 play important roles in wound healing. We, thus, measured the concentrations of IL-6 and TGF-β1 by enzyme-linked immunosorbent assay (ELISA) in wounds of diabetic mice.

In vehicle-treated db/db mice, IL-6 was elevated throughout the course of the study (FIG. 3a). Treatment with either ND-336 or MMP-8 significantly reduced IL-6, and combination of ND-336 and MMP-8 decreased IL-6 the most (FIGS. 3a and 3b). Likewise, treatment with ND-336, MMP-8, or combined ND-336 and MMP-8 significantly reduced the levels of TGF-β1 (FIGS. 3c and 3d).

Figure 8:
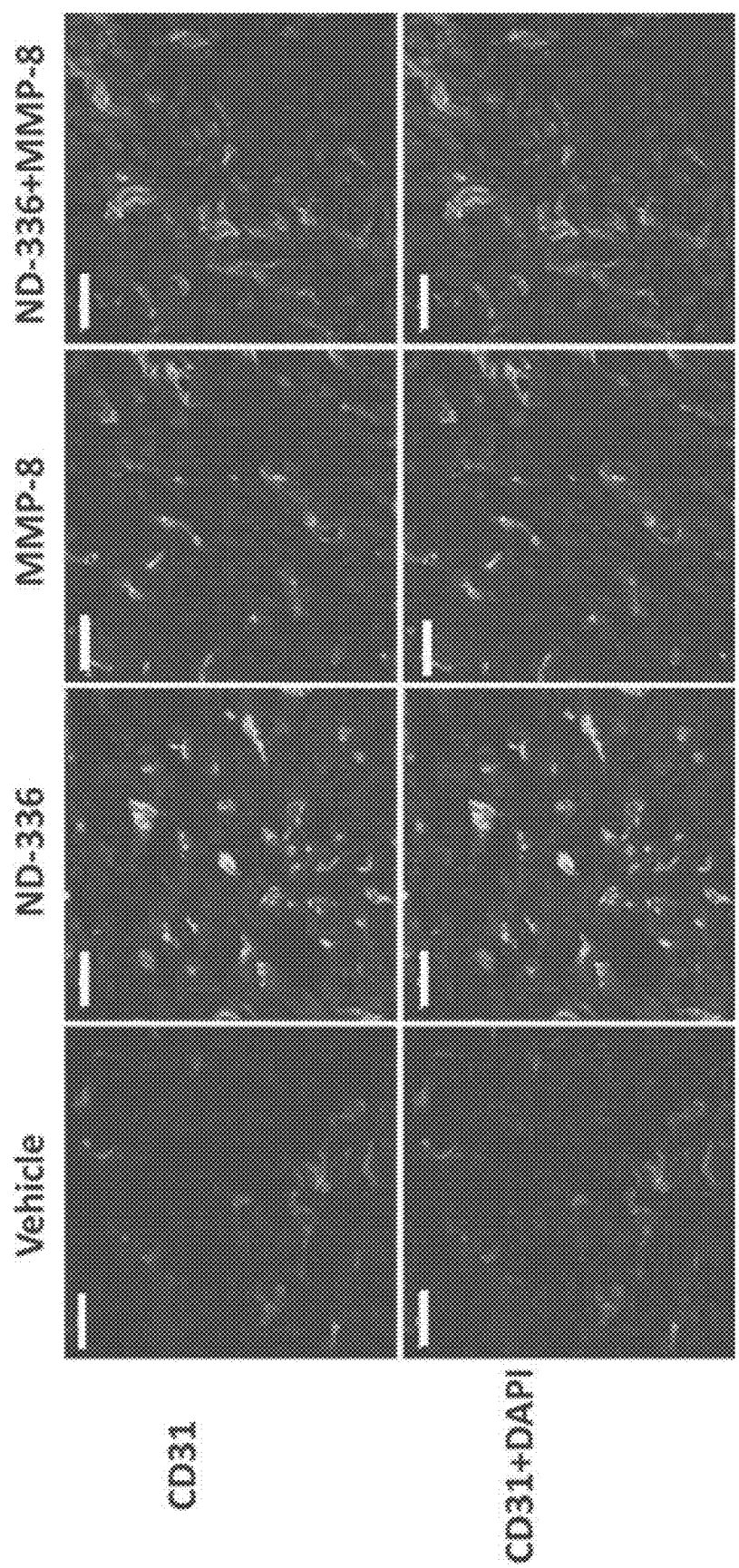
FIG. 8. MMP-9 inhibition, exogenous MMP-8 treatment, and combined MMP-9 inhibition and exogenous MMP-8 increase angiogenesis as measured by anti-CD31.

Angiogenesis is essential for wound healing, facilitating debris removal and granulation tissue development that facilitate wound closure. Cluster of differentiation 31 (CD31) is found on the surface of endothelial cells and it is a widely used marker for angiogenesis. Using anti-CD31 antibodies we found increased angiogenesis in the ND-336, MMP-8, and combined ND-336 plus MMP-8 groups (FIG. 8). Angiogenesis was quantified using vascular endothelial growth factor (VEGF), which enhances vascular permeability, promoting formation of new blood vessels. The levels of VEGF were determined as a function of time after wound infliction. Treatment with ND-336, MMP-8, or combined ND-336 and MMP-8 increased VEGF concentrations in the wounds compared to vehicle (FIGS. 3e and 3f). Our results are in agreement with the increased VEGF levels in human wound fluid (Nissen et al. (1998)*Am J Pathol* 152(6):1445-1452) and in epidermal keratinocytes (Ferrara et al. (2003) *Nat Med* 9(6):669-676).

In summary, we have shown that MMP-9 inhibitors such as the novel MMP-9 inhibitor ND-336 accelerates diabetic wound healing by decreasing inflammation and by enhancing angiogenesis and re-epithelialization of the wound, thus, reversing the pathological condition. Topical administration of active recombinant MMP-8 accelerated diabetic wound healing, resulting in complete re-epithelialization, diminished inflammation, and enhanced angiogenesis. The combination of a selective MMP-9 inhibitor with added MMP-8 was the best strategy to accelerate diabetic wound healing and can significantly improve the treatment of diabetic wounds. These compositions and methods described herein thus provide an effective pharmacological treatment for the healing diabetic wounds.

Accordingly, the combination of a selective MMP-9 inhibitor such as ND-336 and the enzyme MMP-8 accelerates diabetic wound healing, and in particular, accelerates re-epithelialization. MMP-8 was found to accelerate the healing of wounds in both diabetic and non-diabetic subjects, and both chronic and acute wounds. Additionally, the administration of a selective MMP-9 inhibitor can further enhance the healing of a wound exogenously treated with MMP-8.

Compositions and Methods of Treatment

Based on the analysis described herein, it has been discovered that administration of MMP-8 accelerates the healing of wounds, in both diabetic and non-diabetic subjects. Further administration of a selective MMP-9 inhibitor in conjunction with the administration of MMP-8 further enhances the healing of a wound. An MMP-9 inhibitor used in a composition or method with MMP-8 can be a compound of Formula XI:

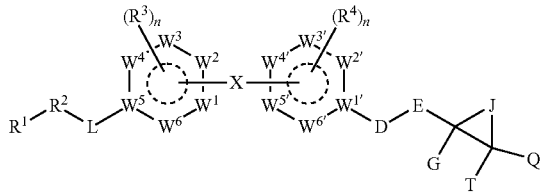

(XI)

wherein
- R¹ is $(C_1-C_6)$alkyl, halo$(C_1-C_6)$alkyl, $(C_1-C_6)$alkoxy, aryl $(C_1-C_6)$alkyl, heteroaryl$(C_1-C_6)$alkyl, aryl$(C_1-C_6)$alkoxy, heteroaryl$(C_1-C_6)$alkoxy, aryl, heteroaryl, hydroxy, $SR^5$, $NR^5R^5$, or absent;
- R² is $CH_2$, carbonyl, $SO_2$, H, or OH;
- L is $CH_2$, $NR^5$, O, or a direct bond;
- $W^1$-$W^6$ are each independently C, N, O, S, or absent, and form a 5 or 6 membered aryl, heterocycle, or heteroaryl ring;
- $W^{1'}$-$W^{6'}$ are each independently C, N, O, S, or absent, and form a 5 or 6 membered aryl, heterocycle, or heteroaryl ring;
- the dashed circles within the rings formed by $W^1$-$W^6$ and $W^{1'}$-$W^{6'}$ denote optional double bonds of the rings formed by $W^1$-$W^6$ and $W^{1'}$-$W^{6'}$;
- R³ and R⁴ are each independently hydroxy, $(C_1-C_6)$alkyl, $(C_1-C_6)$alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^5$, $SO_2N(R_5)_2$, $NR^5R^5$, or $COOR^5$;
- each n is independently 0 to 4;
- each $R^5$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or a nitrogen protecting group;
- X is O, S, SO, $SO_2$, $CH_2$—O, $CH_2$—S, $CH_2$—$NR^5$, $NR^5$, carbonyl, or a direct bond;
- D is S, SO, $SO_2$, P(O)OH, P(O)O$(C_1-C_6)$alkyl, P(O$(C_1-C_6)$alkyl)$_2$, C=N—OH, or carbonyl;
- E is a direct bond, $(C_1-C_6)$alkyl, $(C_3-C_8)$cycloalkyl, $(C_2-C_6)$alkenyl, $(C_2-C_6)$alkynyl, or $(C_3-C_8)$heterocycle;
- J is S, O, or $NR^5$;
- G, T, and Q are each independently H, $(C_1-C_6)$alkyl, or cyano;
- any alkyl, amino, aryl, heteroaryl, or cycloalkyl is optionally substituted with 1 to about 5 $(C_1-C_6)$alkyl, $(C_1-C_6)$alkoxy, aryl, heteroaryl, aryl$(C_1-C_6)$alkyl, heteroaryl$(C_1-C_6)$alkyl, nitro, halo, amino, or hydroxy groups;
- or a pharmaceutically acceptable salt thereof. In some embodiments, when L is $CH_2$ or O, and R² is $CH_2$, R¹ is not $(C_1-C_6)$alkyl; when L is O and R² is carbonyl, R¹ is not $(C_1-C_6)$alkyl; and/or when L is $NR^5$, R² is $CH_2$.

An MMP-9 inhibitor used in a composition or method with MMP-8 can also be a compound of Formula XII:

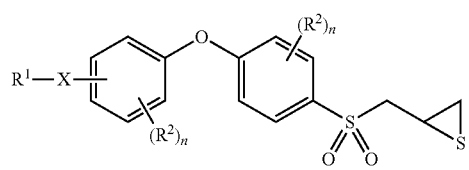

(XII)

wherein
- X is O, —S—NH—, NW wherein $R^a$ is H or $(C_1-C_4)$ alkyl;
- R¹ is a solubilizing group comprising 5-30 atoms, in addition to hydrogen, selected from carbon, oxygen, nitrogen, sulfur, and phosphorus;
- each R² is independently hydroxy, $(C_1-C_6)$alkyl, $(C_1-C_6)$ alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^z$, $SO_2N(R^z)_2$, $NR^zR^z$, or $COOR^z$; wherein each $R^z$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl$(C_1-C_6)$alkyl, or optionally a nitrogen protecting group when $R^z$ is covalently bonded to a nitrogen atom; and
- each n is independently 0, 1, 2, 3, or 4;
- or a salt or solvate thereof. The compound can have an aqueous solubility of at least 5 mg/mL.

An MMP-9 inhibitor used in a composition or method with MMP-8 can also be a compound of Formula XIII:

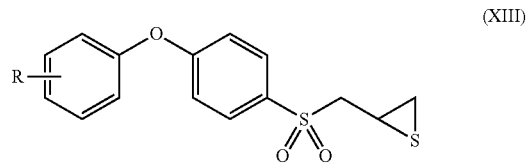

(XIII)

wherein R is H, OH, $NH_2$, NH-amino acid, or —X—(C=O)—R' where X is O or NH, and R' is alkyl, aryl, alkylaryl, amino, or alkoxy, where any alkyl, aryl, or amino is optionally substituted.

An MMP-9 inhibitor used in a composition or method with MMP-8 can also be a compound of Formula XIV:

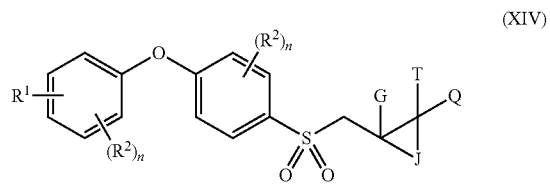

(XIV)

wherein
- R¹ is —$CH_2$—$NHR^a$ wherein $R^a$ is H or $(C_1-C_6)$alkanoyl; —NH—C(=NH)—$NH_2$; or

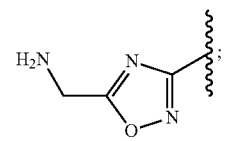

- J is S or O;
- G, T, and Q are each independently H, $(C_1-C_6)$alkyl, or —CN;
- each R² is independently H, OH, $(C_1-C_6)$alkyl, $(C_1-C_6)$ alkoxy, $(C_1-C_6)$alkanoyl, $(C_1-C_6)$alkanoyloxy, aryl, heteroaryl, carboxy, cyano, nitro, halo, trifluoromethyl, trifluoromethoxy, $SR^z$, $SO_2N(R^z)_2$, $NR^zR^z$, or $COOR^z$; wherein each $R^z$ is independently H, $(C_1-C_6)$alkyl, $(C_1-C_6)$alkanoyl, $(C_6-C_{10})$aroyl, aryl, aryl$(C_1-C_6)$alkyl, heteroaryl, heteroaryl($C_1$-$C_6$)alkyl, or optionally a nitrogen protecting group when $R^z$ is covalently bonded to a nitrogen atom; and each n is independently 0, 1, 2, 3, or 4;

or a salt or solvate thereof.

Preferably, the MMP-9 inhibitor of Formula XI-XIV is selective for MMP-9 over MMP-8, wherein the Ki value of the inhibitor for MMP-9 is at least 0.5 µM smaller than the Ki value of the inhibitor for MMP-8.

Table 1 provides several specific MMP-9 inhibitors that can be administered in conjunction with the compositions and methods of the invention, such as the exogenous application of MMP-8 to a wound. MMP-9 inhibitors that are selective for MMP-9 relative to MMP-8 (e.g., having a difference in Ki of greater than about 0.5 µM, greater than about 1.0 µM, greater than about 1.5 µM, greater than about 2 µM, greater than about 5 µM, or greater than about 7 µM; selective for MMP-9) are particularly effective.

TABLE 1

Thiiranes with MMP-9 Selectivity Relative to MMP-8.

| Name | Structure | $K_i$ MMP-9 | $K_i$ MMP-8 |
|---|---|---|---|
| SB-3CT | (structure) | $K_i$ = 0.40 ± 0.15 µM slow-binding residence time = 13.4 min | $K_i$ = 2.1 ± 0.4 µM linear non-competitive |
| ND-322 | (structure) | $K_i$ = 0.40 ± 0.15 µM slow-binding residence time = 31.4 min | $K_i$ = 2.6 ± 0.4 µM linear non-competitive |
| ND-364 | (structure) | $K_i$ = 0.13 ± 0.01 µM non-competitive | $K_i$ = 3.4 ± 0.4 µM non-competitive |
| p-OH SB-3CT | (structure) | $K_i$ = 0.16 ± 0.02 µM slow-binding residence time = 24.5 min | $K_i$ = 2.6 ± 0.3 µM non-competitive |
| ND-336 | (structure) | $K_i$ = 0.15 ± 0.01 µM slow-binding residence time = 47.3 min | $K_i$ = 7.7 ± 0.1 µM non-competitive |
| ND-380 | (structure) | $K_i$ = 0.18 ± 0.03 µM slow-binding residence time = 19.6 min | $K_i$ = 13 ± 2 µM non-competitive |
| ND-394 | (structure) | $K_i$ = 0.86 ± 0.11 µM slow-binding residence time = 25.6 min | $K_i$ = 15 ± 3 µM non-competitive |
| ND-364 | (structure) | $K_i$ = 0.093 ± 0.008 µM slow-binding residence time = 47.0 min | $K_i$ = 0.73 ± 0.05 µM competitive |

TABLE 1-continued

Thiiranes with MMP-9 Selectivity Relative to MMP-8.

| Name | Structure | MMP-9 | $K_i$ MMP-8 |
| --- | --- | --- | --- |
| ND-395 | 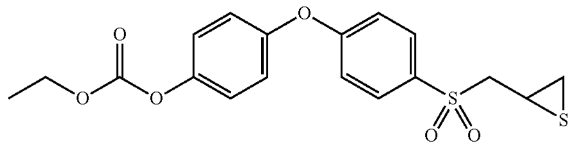 [SMILES: CCOC(=O)Oc1ccc(Oc2ccc(S(=O)(=O)CC3CS3)cc2)cc1] | $K_i = 0.93 \pm 0.02$ μM<br>slow-binding<br>residence time = 119 min | $K_i = 11 \pm 3$ μM |
| JNMS-38 | 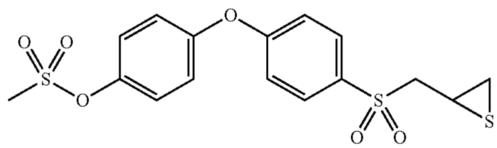 [SMILES: CS(=O)(=O)Oc1ccc(Oc2ccc(S(=O)(=O)CC3CS3)cc2)cc1] | $K_i = 0.005 \pm 0.001$ μM<br>slow-binding<br>residence time = 152 min | $K_i = 1.4 \pm 0.48$ μM<br>linear competitive |

Additional MMP-9 inhibitors, including MMP-9 inhibitors that are selective for MMP-9 relative to MMP-8, are further described in U.S. Pat. No. 6,703,415 (Mobashery et al.); U.S. Pat. No. 7,114,917 (Mobashery et al.); U.S. Pat. No. 7,928,127 (Lee et al.), U.S. Pat. No. 8,093,287 (Lee et al.); and U.S. Pat. No. 8,937,151 (Chang et al.); U.S. Patent Publication No. 2013/0064878 (Chang et al.); and International Publication No. WO 2015/127302 (Chang et al.), which patent documents are incorporated herein by reference, and wherein the compound formulas and individual compounds are individually incorporated herein by reference.

Preferably, the selective MMP-9 inhibitor has a long residence time (e.g., greater than 10 minutes, greater than 15 minutes, greater than 20 minutes, greater than 30 minutes, greater than 45 minutes, or greater than 100 minutes) with respect to MMP-9. The selective MMP-9 inhibitory is also preferably a slow-binding inhibitor of MMP-9, and/or a competitive inhibitor of MMP-8 (i.e., very little or no residence time with respect to MMP-8).

Accordingly, the invention provides a pharmaceutical composition comprising MMP-8 and a pharmaceutically acceptable diluent, carrier, or excipient. The MMP-8 can be a recombinant MMP-8. The composition that includes MMP-8 can be used to treat a wound in a mammal by topically applying the composition to the wound. The amount of MMP-8 can be at least about 0.5 μg per 50 mm$^2$ of open wound per day. Greater amounts of MMP-8 can also be used, such as 1 μg per 50 mm$^2$ of open wound, 1.5 μg per 50 mm$^2$ of open wound, 2 μg per 50 mm$^2$ of open wound, 2.5 μg per 50 mm$^2$ of open wound, or 5 μg per 50 mm$^2$ of open wound, or even greater amounts. Such doses can be applied once per day, or multiple times per day. The dose can also be divided and applied at various times throughout the day.

A subject that has a wound can be administered an MMP-8 composition in combination with administration of an MMP-9 inhibitor, orally, intraperitoneally, or topically. The MMP-9 inhibitor can be a selective MMP-9 inhibitor (e.g., selective for MMP-9 over MMP-8). The amount of the MMP-9 inhibitor can be at least about 0.05 mg per 50 mm$^2$ of open wound per day. Greater amounts of the MMP-9 inhibitor can also be used, such as 0.1 mg per 50 mm$^2$ of open wound, 0.2 mg per 50 mm$^2$ of open wound, 0.25 mg per 50 mm$^2$ of open wound, 0.5 mg per 50 mm$^2$ of open wound, or 1 mg per 50 mm$^2$ of open wound, or even greater amounts. Such doses can be applied once per day, or multiple times per day. The dose can also be divided and applied at various times throughout the day.

In one embodiment, the MMP-9 inhibitor is SB-3CT. In another embodiment, the MMP-9 inhibitor is ND-322. In another embodiment, the MMP-9 inhibitor is ND-364. In another embodiment, the MMP-9 inhibitor is p-OH SB-3CT. In another embodiment, the MMP-9 inhibitor is ND-336. In another embodiment, the MMP-9 inhibitor is ND-380. In another embodiment, the MMP-9 inhibitor is ND-394. In another embodiment, the MMP-9 inhibitor is ND-364. In another embodiment, the MMP-9 inhibitor is ND-395. In yet another embodiment, the MMP-9 inhibitor is JNMS-38. In further embodiments, the administration of one MMP-9 inhibitor can be accompanied by the administration of one or more other of the aforementioned MMP-9 inhibitors.

Pharmaceutical Formulations

The compounds (e.g., MMP-8 and/or inhibitors of MMP-9) described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds, enzymes, or compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can be used to treat a wound in an animal, such as a mammal. A mammal includes a primate, human, rodent, canine, feline, bovine, ovine, equine, swine, caprine, bovine and the like.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Abbreviations.

ADAM, a disintegrin and metalloproteinase; AUC, area-under-the-curve; Boc, t-Butoxycarbonyl; m-CPBA, meta-chloroperbenzoic acid; DMF, dimethylformamide; DMSO, dimethyl sulfoxide; ESI, electrospray ionization; IL-6, interleukin-6; MMP, matrix metalloproteinase; MOCAc, (7-methoxycoumarin-4-yl)acetyl; PBS, phosphate buffered saline; THF, tetrahydrofuran; TIMP, tissue inhibitor of metalloproteinase; TGF-β1, transforming growth factor β1; TLC, thin-layer chromatography; TUNEL, terminal deoxynucleotidyl transferase-mediated DUTP-nick-end labeling; UPLC, ultra-performance liquid chromatography; VEGF, vascular endothelial growth factor.

Example 1. Synthesis and Analysis of MMP Inhibitors

Synthesis of ND-336.

The synthesis of ND-336 is shown in Scheme 1. The reaction of 4-mercaptophenol (2) with allyl bromide (1) produced compound 3, which was allowed to react with 4-fluorobenzonitrile to afford diphenyl ether 4 in good yields (94% and 82% for the first and second steps, respectively). Subsequent reduction of the nitrile with LiAlH$_4$, followed by Boc-protection of the resultant amine yielded compound 5, which was oxidized to the corresponding oxirane 6. The reaction of 6 with thiourea produced the Boc-protected thiirane 7. After the final acid Boc-deprotection, the desired ND-336 was in hand as the HCl salt.

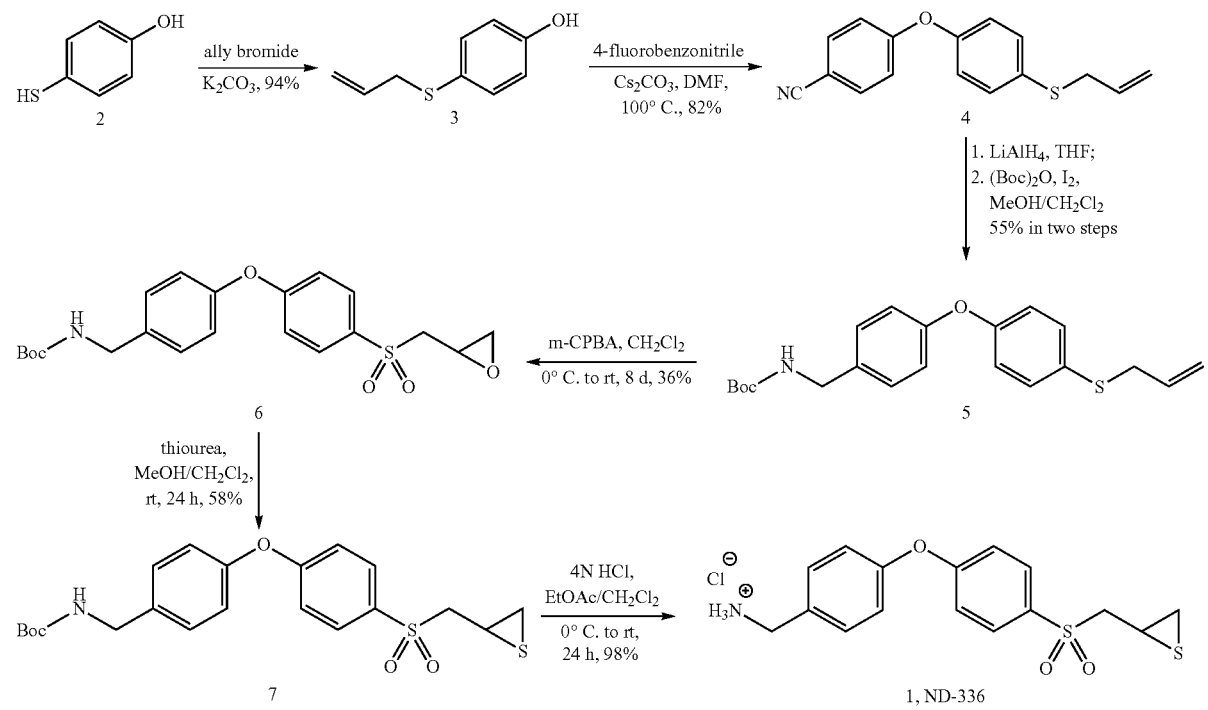

Scheme 1. Synthesis of ND-336

Other MMP-9 inhibitors can be prepared by the methods described in U.S. Pat. No. 6,703,415 (Mobashery et al.); U.S. Pat. No. 7,114,917 (Mobashery et al.); U.S. Pat. No. 7,928,127 (Lee et al.), U.S. Pat. No. 8,093,287 (Lee et al.); and U.S. Pat. No. 8,937,151 (Chang et al.); U.S. Patent Publication No. 2013/0064878 (Chang et al.); and International Publication No. WO 2015/127302 (Chang et al.); each incorporated herein by reference.

Chemistry.

All reactions were performed under nitrogen atmosphere, unless otherwise noted. $^1$H and $^{13}$C NMR spectra were recorded on Varian INOVA-500 or Varian UnityPlus 300 spectrometer (Varian Inc., Palo Alto, Calif., USA), Bruker AVANCE III HD 500 or Bruker AVANCE III HD 400 (Bruker Corporation, Billerica, Mass., USA). TLC silica gel 60 F$_{254}$ aluminum sheets (EMD Millipore Corporation, Billerica, Mass., USA) were used for thin-layer chromatography. Flash chromatography was performed with an automated chromatograph system: Combiflash RF 200i UV/Vis (Teledyne Isco, Lincoln, Nebr., USA). High-resolution mass spectra were obtained by ESI ionization using a BrukermicrOTOF/Q2 mass spectrometer (BrukerDaltonik, Bremen, Germany). Purity of the prepared compounds was in general >95%, as confirmed by UPLC. Conditions are detailed in the UPLC section. 4-(Allylthio)phenol (3) was prepared as previously described (Ikejiri M, et al. (2005) *J Biol Chem* 280(40):33992-34002; Goux et al. (1994) *Tetrahedron* 50(34):10321-10330).

4-(4-(Allylthio)phenoxy)benzonitrile (4)

A mixture of 3 (1.45 g, 8.72 mmol), 4-fluorobenzonitrile (1.01 g, 8.38 mmol), and $Cs_2CO_3$ (4.26 g, 13.1 mmol) in DMF (50 mL) was heated at 100° C. for 3.5 h. After the addition of saturated aqueous LiBr (250 mL), the mixture was extracted with hexanes/EtOAc (9:1). The combined organic layers were washed with water and brine, dried over anhydrous $Na_2SO_4$, and concentrated under reduced pressure. The resultant residue was purified by silica gel chromatography (hexanes/EtOAc, 97:3) to give 4 (1.84 g, 82%) as an oil. $^1$H NMR (300 MHz, $CDCl_3$) δ 7.77-7.52 (m, 2H), 7.49-7.30 (m, 2H), 7.14-6.82 (m, 4H), 5.87 (ddt, J=16.9, 10.0, 6.9 Hz, 1H), 5.29-4.93 (m, 2H), 3.53 (dt, J=6.9, 1.1 Hz, 2H). $^{13}$C NMR (126 MHz, $CDCl_3$) δ 161.6, 153.9, 134.4, 133.7, 132.7, 132.4, 121.0, 119.0, 118.2, 118.1, 106.3, 38.2. HRMS (ESI$^+$, m/z): calcd for $C_{16}H_{14}NO$ [M+H]$^+$, 268.0791. found, 268.0799.

t-Butyl 4-(4-(allylthio)phenoxy)benzylcarbamate (5)

A solution of compound 4 (4.98 g, 18.63 mmol) in THF (78 mL) was added dropwise to $LiAlH_4$ (2.12 g, 55.89 mmol) in THF (78 mL) at 0° C. over a period of 30 min. The ice-bath was removed and the reaction mixture was stirred at room temperature for 1.5 h at which point the TLC showed the reaction to be complete. The solution was cooled again in ice-water temperature and quenched carefully with the dropwise addition of 2.4 mL water, 2.4 mL 15% aqueous NaOH, and 7.2 mL water. The solution was gradually warmed to room temperature and stirred for 30 min, filtered through a celite pad, extracted with diethyl ether and EtOAc. The combined organic layer was washed with water and brine, and the solution was dried over anhydrous $Na_2SO_4$. The solvent was evaporated under reduced pressure to give the crude primary amine, which was used directly in the next step.

To a mixture of amine (4.3 g, 15.84 mmol) and (Boc)$_2$O (5.2 g, 23.77 mmol) in MeOH/$CH_2Cl_2$ (3:2, 150 mL), was added a catalytic amount of iodine (402 mg, 1.58 mmol, 10 mol %). After stirring the reaction mixture for 24 h at room temperature, the solvent was evaporated in vacuo, and EtOAc was added. The solution was washed with 5% aqueous $Na_2S_2O_3$ and saturated $NaHCO_3$, and dried over anhydrous $Na_2SO_4$. The solvent was evaporated in vacuo, and the residue was purified by silica gel chromatography (hexanes/EtOAc, 95:5) to afford compound 4 (3.21 g, 55% in two steps). $^1$H NMR (300 MHz, $CDCl_3$) δ 7.38-7.32 (m, 2H), 7.31-7.25 (m, 2H), 6.99-6.90 (m, 4H), 6.17-6.09 (m, 1H), 5.08-5.03 (m, 2H), 4.85 (s, b, 1H), 4.29 (d, J=3.0 Hz, 2H), 3.49-3.47 (m, 2H), 1.46 (s, 9H). $^{13}$C NMR (75 MHz, $CDCl_3$) δ 156.8, 156.4, 156.1, 134.0, 133.2, 131.4, 131.2, 129.2, 127.2, 119.3, 117.7, 79.7, 44.4, 38.8, 28.6. HRMS (ESI$^+$, m/z): calcd for $C_{21}H_{25}NNaO_3S$ [M+Na]$^+$, 394.1447. found, 394.1472.

t-Butyl 4-(4-((oxiran-2-ylmethyl)sulfonyl)phenoxy)benzylcarbamate (6)

m-CPBA (2.03 g, 11.8 mmol) was added in batches to a solution of 5 (0.88 g, 2.36 mmol) in $CH_2Cl_2$ (8 mL) immersed in an ice-water bath. After completion of the addition, the ice-water bath was removed and the solution was stirred at room temperature for 3 d. Another batch of m-CPBA (1.02 g, 5.89 mmol) was added, and the mixture was stirred at room temperature for an additional 5 d. The suspension was filtered, and the filtrate was diluted with $CH_2Cl_2$ and washed with 10% aqueous sodium thiosulfate, followed by saturated $NaHCO_3$ and brine. The organic layer was dried over anhydrous $Na_2SO_4$, the suspension was filtered, and the solution was concentrated in vacuo. The product was purified by silica gel chromatography (hexanes/EtOAc, 2:1 to 1:1) to yield 6 (0.36 g, 36%). $^1$H NMR (400 MHz, $CDCl_3$) δ 7.91-7.65 (m, 2H), 7.27-7.25 (m, 2H), 7.06-6.95 (m, 4H), 5.22 (s, b, 1H), 4.24 (d, J=5.1 Hz, 2H), 3.44-3.02 (m, 3H), 2.72 (dd, J=8.0, 2.0 Hz, 1H), 2.39 (dd, J=4.8, 2.0 Hz, 1H), 1.39 (s, 9H). $^{13}$C NMR (100 MHz, $CDCl_3$) δ 163.0, 154.1, 136.6, 130.7, 129.5, 123.2, 120.7, 118.0, 117.8, 79.7, 59.8, 46.04, 45.99, 44.1, 28.6. HRMS (ESI$^+$, m/z): calcd for $C_{21}H_{25}NNaO_6S$ [M+Na]$^+$, 442.1295. found, 442.1292.

t-Butyl 4-(4-((thiiran-2-ylmethyl)sulfonyl)phenoxy)benzylcarbamate (7)

Thiourea (55.3 mg, 0.73 mmol) was added to a solution of compound 6 (138.4 mg, 0.33 mmol) in MeOH/$CH_2Cl_2$ (1:1, 3 mL), and the resulting mixture was stirred at room temperature for 24 h. The solvent was removed under reduced pressure and the residue was partitioned between $CH_2Cl_2$ and water. The organic layer was washed with water and brine, dried over anhydrous $Na_2SO_4$, and filtered. Evaporation of the solvent gave the crude product, which was purified by silica gel chromatography (83.4 mg, 58%). $^1$H NMR (300 MHz, $CDCl_3$) δ 7.85 (d, J=8.7 Hz, 2H), 7.33 (d, J=8.7 Hz, 2H), 7.13-6.97 (m, 4H), 4.95 (s, b, 1H), 4.33 (d, J=5.9 Hz, 2H), 3.51 (dd, J=14.1, 5.7 Hz, 1H), 3.17 (dd, J=14.1, 7.8 Hz, 1H), 3.11-2.98 (m, 1H), 2.53 (dd, J=6.3, 1.6 Hz, 1H), 2.15 (dd, J=5.1, 1.6 Hz, 1H), 1.46 (s, 9H). $^{13}$C NMR (75 MHz, $CDCl_3$) δ 163.1, 156.0, 154.0, 136.3, 132.1, 130.8, 129.4, 120.7, 117.8, 79.8, 62.8, 44.1, 28.5, 26.2, 24.4. HRMS (ESI$^+$, m/z): calcd for $C_{21}H_{25}NNaO_5S_2$ [M+Na]$^+$, 458.1066. found, 458.1089.

(4-(4-((Thiiran-2-ylmethyl)sulfonyl)phenoxy)phenyl)methanamine HCl salt (1)

HCl (0.7 mL, 4 N in 1,4-dioxane) was added to a solution of thiirane 7 (61.0 mg, 0.14 mmol) in $CH_2Cl_2$/EtOAc (1:1, 4 mL). After stirring at room temperature for 24 h, the mixture was concentrated under reduced pressure. The resulting crude compound was triturated with diethyl ether, and the product was obtained by filtration (51.0 mg, 98%). $^1$H NMR (300 MHz, $CD_3OD$) δ 7.93 (d, J=8.6 Hz, 2H), 7.58 (d, J=8.6 Hz, 2H), 7.19 (d, d, J=8.4 Hz, 4H), 4.16 (s, 2H), 3.57-3.43 (m, 2H), 3.11-2.99 (m, 1H), 2.52 (dd, J=6.3, 1.4 Hz, 1H), 2.14 (dd, J=5.1, 1.4 Hz, 1H). $^{13}$C NMR (75 MHz, $CD_3OD$) δ 162.5, 156.2, 133.0, 131.3, 131.1, 130.0, 120.7, 118.2, 62.0, 42.6, 25.8, 23.0. HRMS (ESI$^+$, m/z): calcd for $C_{16}H_{18}NO_3S_2$ [M+H]$^+$, 336.0723. found, 336.0709. The purity of ND-336 was >95%, as determined by UPLC with UV detection.

Water-Solubility Determination.

A saturated aqueous solution of ND-336 was prepared and the solution was filtered. A 100-fold dilution of the filtrate was analyzed by UPLC with UV detection (see conditions below) using peak area and linear regression parameters calculated from a calibration curve. The calibration curve was prepared using known concentrations of ND-336 in acetonitrile. The assay was linear from 0.5 to 100 μg/mL with $R^2$ value of 0.999. The water solubility of ND-336 is 4.90±0.06 mg/mL.

Ultra Performance Liquid Chromatography (UPLC).

A Waters Acquity UPLC System (Waters Corporation, Milford, Mass., USA) equipped with a binary solvent manager, an autosampler, a column heater, and a photodiode array detector was used to test the purity and water solubility of ND-336. An Acquity UPLC® HSS C18 column (1.8 µm, 2.1×100 mm, Waters Corporation, Milford, Mass., USA) was used. The mobile phase consisted of water (A) and acetonitrile (B) elution at 0.5 mL/min with 85% A, 15% B for 2 min, followed by a 5-min linear gradient to 5% A, 95% B, then 5% A, 95% B for 2 min, followed by a 1-min linear gradient back to 85% A, 15% B and then 85% A, 15% B for 1 min. ND-336 was detected by UV at 245 nm. The retention time was 4.33 min.

Example 2. Acceleration of Diabetic Wound Healing Using a Novel Protease-Anti-Protease Combination Therapy Enzyme Inhibition Studies.

Human recombinant active MMP-2 and MMP-7, and the catalytic domains of MMP-3 and MMP-14/MT1-MMP were purchased from EMD Chemicals, Inc. (San Diego, Calif., USA); human recombinant catalytic domains of MMP-1, MMP-8, and MMP-9 were purchased from Enzo Life Sciences, Inc. (Farmingdale, N.Y., USA); human recombinant active ADAM9 and ADAM10 were purchased from R&D Systems (Minneapolis, Minn., USA). Fluorogenic substrates MOCAc-Pro-Leu-Gly-Leu-A2pr(Dnp)-Ala-Arg-$NH_2$ (for MMP-2, MMP-7, MMP-9 and MMP-14) and MOCAc-Arg-Pro-Lys-Pro-Val-Glu-Nva-Trp-Arg-Lys(Dnp)-$NH_2$ (for MMP-3) were purchased from Peptides International (Louisville, Ky., USA); Mca-KPLGL-Dpa-AR-$NH_2$ (for MMP-1, MMP-8 and ADAM10) and Mca-PLAQAV-Dpa-RSSSR-$NH_2$ (for ADAM9) were purchased from R&D Systems (Minneapolis, Minn., USA). The $K_m$ values for MMP-2, MMP-9 and MMP-14 were the same as previously reported by Gooyit et al. ((2013) *J. Med. Chem.* 56(20):8139-8150). Inhibitor stock solutions (10 mM) were prepared freshly in DMSO before enzyme inhibition assays. We followed the same methodology for enzyme inhibition studies as reported before by Page-McCaw et al. ((2007) *Nat Rev Mol Cell Biol* 8(3):221-233). Enzyme inhibition studies were carried out using a Cary Eclipse fluorescence spectrophotometer (Varian, Walnut Creek, Calif., USA). Compound 1 was stable in the buffers used in the kinetic assays.

Animals.

Female diabetic db/db mice (BKS.Cg-Dock7$^m$+/+Lepr$^{db}$/J, 8-weeks old) were purchased from the Jackson Laboratory (Bar Harbor, Me., USA) and fed 5001 Laboratory Rodent Diet (LabDiet, St. Louis, Mo., USA) and water ad libitum. Mice were housed in polycarbonate shoebox cages with hardwood bedding at 72±2° F. and 12 h light/12 h dark.

Excisional Diabetic Wound Model.

The dorsal area of the mice was shaved, and a single excisional 8-mm diameter wound (50 mm$^2$) was made on the dorsal thorax with a biopsy punch (Miltex, Plainsboro, N.J., USA) while the animals were under isofluorane anesthesia. Wounds were covered with Tegaderm™ dressing (3M Company, St. Paul, Minn., USA). Topical treatment was started the next day.

Wound Measurements.

Mice were anesthetized with isofluorane, and wounds were photographed with an Olympus SP-800 UZ camera mounted on a tripod at a fixed distance; a ruler was included in the digital photo. Wound areas were calculated using NIH ImageJ software (version 1.48) and expressed as percent change in wound area relative to day 0.

ND-336 Diabetic Wound Healing Study.

For this study, db/db mice were divided into two groups (n=8 mice per group): vehicle (50 µL of 20% DMSO, 80% propylene glycol per wound per day) and ND-336 (50 µL of a 2 mg/mL solution of ND-336 in 20% DMSO/80% propylene glycol, equivalent to 0.1 mg/wound/day). Wound measurements were taken on days 0, 7, 10, and 14. Animals were sacrificed on day 14 and wounds analyzed by H&E staining, TUNEL, and in-situ zymography.

Exogenous MMP-8 Study.

Female diabetic db/db (BKS.Cg-Dock7m+/+Leprdb/J, 8-weeks old, 38±3 g, n=24) were used for this study. Wounds were inflicted as described and the following day the wounds were treated topically with MMP-8 (50 µL of 20 µg/mL MMP-8 in reaction buffer) or vehicle (50 µL reaction buffer) once a day for 14 days. The reaction buffer consisted of 50 mM Tris (pH 7.5), 10 mM $CaCl_2$, 150 mM NaCl, and 0.05% (w/v) Brij-35 (polyoxyethyleneglycoli dodecyl ether). Digital photographs of the wounds were taken on days 0, 7, 10, and 14 while animals were under isoflurane anesthesia. On days 7 and 14, 12 mice (n=6 per group) were sacrificed. The wounds were excised, embedded in OCT compound, and cryosectioned for histological evaluation and in-situ zymography.

Combined ND-336 and MMP-8 Study.

Female db/db mice (n=6 per group) were divided into four groups: vehicle (50 µL of 10% DMSO/10% propylene glycol/80% saline per wound per day dosed in the morning and 50 µL of reaction buffer (50 mM Tris (pH 7.5), 10 mM $CaCl_2$, 150 mM NaCl, and 0.05% (w/v) Brij-35) per wound per day dosed in the afternoon), ND-336 (50 µL of 1 mg/mL ND-336 (equivalent to 0.05 mg/wound/day) in 10% DMSO/10% propylene glycol/80% saline dosed in the morning and 50 µL of reaction buffer dosed in the afternoon), MMP-8 (50 µL of 10% DMSO/10% propylene glycol/80% saline per wound per day dosed in the morning and 50 µL of 20 µg/mL of MMP-8 in reaction buffer (equivalent to 1 µg/wound/day) dosed in the afternoon), and combined ND-336 and MMP-8 (0.05 mg of ND-336 in 50 µL of 10% DMSO/10% propylene glycol/80% saline per wound per day dosed in the morning and 1 µg of MMP-8 in 50 µL of reaction buffer per wound per day dosed in the afternoon). Mice were sacrificed on days 7, 10, and 14, and the excised wounds were embedded in OCT compound and cryosectioned for histological evaluation and in situ zymography.

Measurement of IL-6, TGF-β1, and VEGF by ELISA.

Wound tissues (n=3 mice/group) were harvested and immediately frozen in liquid nitrogen on days 1, 3, and 14. The extracted tissues were homogenized in cold lysis buffer containing free-EDTA protease inhibitor cocktail (Pierce, Rockford, Ill., USA). The lysates were analyzed for protein concentration by the Bradford protein assay (Bio-Rad, Hercules, Calif., USA). The levels of IL-6, TGF-β1 and VEGF in the lysates were determined by ELISA, following the manufacturer's protocol (Abcam, Cambridge, Mass., USA). The cytokine levels for each mouse sample were expressed in picograms/mg tissue.

Statistical Analyses.

Data were analyzed for statistical significance using the Student t-test (Excel) using a two-tail distribution and unequal variance.

MMP-9 Knockout Study.

Female MMP-9 knockout mice (B6.FVB(Cg)-Mmp9$^{tm1Tvu}$/J, 8-weeks old, 19±2 g, n=14) and wild-type mice ($C_{57}$BLKS/6J, 8-weeks old, 19±2 g, n=14, same background as MMP-9 knockout mice) were used. The mice were acclimated to the study room for one week prior to commencement of the study. Diabetes was induced by intraperitoneal injection of streptozotocin (Sigma-Aldrich, St. Louis, Mo.) at 150 mg/kg. Streptozotocin was dissolved in 100 mM sodium citrate buffer (pH 4.5) and administered within 15 min after preparation. After streptozotocin treatment, the mice were housed in disposable cages and given 10% sucrose water to drink for two days. The fasting blood glucose levels were determined two days after streptozotocin treatment. Animals with blood glucose greater than 300 mg/dL were considered diabetic. Animals with blood glucose less than 300 mg/dL received a second dose of streptozotocin one week later. The average blood glucose level of all the animals was determined to be 465±113 mg/dL. Wounds were inflicted as described and digital photographs were taken on days 0, 7, and 14. Mice (n=7 per group) were sacrificed on days 7 and 14, the wounds were excised, embedded in OCT compound, and cryosectioned for histological evaluation. FIG. 4 shows the effect of MMP-9 inhibition on diabetic wound healing. FIG. 5 shows the effect of MMP-9 gene ablation on diabetic wound healing.

Cloning and Purification of Mouse MMP-8 and Effect of MMP-8 on Diabetic Wound Healing.

The gene for the catalytic domain (304-852 bp), without the pro-domain, of MMP-8 was optimized for expression in *Escherichia coli* and was synthesized by GenScript (Piscataway, N.J.) with unique NdeI and XhoI restriction sites flanking the gene at the 5' and 3' termini, respectively. The gene was cloned into vector pET28a. *E. coli* DH5α was transformed by this construct. The recombinant MMP-8 was expressed in *E. coli* BL21 (DE3) and purified using a previously published method (Botos et al. (1999) *J Mol Biol* 292(4):837-844), with induction by 0.5 mM isopropyl β-D-1-thiogalactopyranoside at 20° C. The purity of the protein was determined to be >95% by SDS-PAGE. The enzyme concentration was evaluated spectrophotometrically using the extinction coefficient predicted by ProtParam (Gasteiger et al. (2005) *The Proteomics Protocols Handbook*, ed. Walker J M (Humana Press), pp 571-607) ($\Delta\epsilon_{280}$=19681.6 $M^{-1}$ $cm^{-1}$). Aliquots of the concentrated protein were stored in 50 mM Tris (pH 7.5), 5 mM $CaCl_2$, 300 mM NaCl, 20 μM $ZnCl_2$, 0.5% (w/v) Brij-35, 30% glycerol at −80° C. FIG. 6 shows that topical treatment with exogenously added MMP-8 accelerates wound healing in db/db mice.

Dose-Response Study with ND-336.

We observed that ND-336 at a dose of 0.1 mg/wound/day accelerated diabetic wound healing. In order to find the lowest dose of ND-336 that was efficacious in diabetic wound healing, a dose response study was conducted at 0.05, 0.025, and 0.01 mg of ND-336/wound/day. For this study, db/db mice were divided into four groups: vehicle (50 μL of 20% DMSO/80% propylene glycol, n=7 mice), 0.05 mg/wound/day ND-336 (50 μL of 1 mg/mL ND-336 in 20% DMSO/80% propylene glycol, n=6 mice), 0.025 mg/wound/day ND-336 (50 μL of 0.5 mg/mL ND-336 in 20% DMSO/80% propylene glycol, n=7 mice), 0.01 mg/wound/day ND-336 (50 μL of 0.2 mg/mL ND-336 in 20% DMSO/80% propylene glycol, n=7 mice).

As shown in FIG. 7, on day 14 the 0.05 mg/wound/day group exhibited significant better healing than the vehicle and the 0.025 mg/wound/day and 0.01 mg/wound/day groups. All the subsequent studies were performed at the 0.05 mg/wound/day level.

Histological Evaluation, Apoptosis Detection and In-Situ Zymography.

Wounds were embedded in optimal cutting temperature (OCT, Tissue-Tek, Sakura Finetek, Torrance, Calif., USA) compound and cryosectioned at 12-μm thickness for hematoxylin-eosin (H&E) and at 8-μm thickness for in-situ zymography. Re-epithelialization was assessed on a fluorescent microscope (Nikon Eclipse 90i, Nikon Instruments, Inc., Melville, N.Y., USA). Apoptotic cells in wound sections were assessed using a modified terminal deoxynucleotidyl transferase-mediated dUTP-nick-end labeling (TUNEL) assay kit, following the manufacturer's instructions (Trevigen, Inc., Gaithersburg, Md., USA). For in-situ zymography, unfixed cryostat sections of wound tissues were incubated in reaction buffer (50 mM TBS pH 7.6) containing DQ-gelatin or DQ-collagen (Molecular Probes, Inc., Eugene, Oreg., USA) at 37° C. for 6 h. After fixation in 4% paraformaldehyde in PBS, cells were counterstained with DAPI and the images were visualized by fluorescence microscopy. Immunofluorescent detection of vascular density was performed by staining the tissues with Alexa Fluor 488 anti-mouse CD31 (BioLegend, San Diego, Calif., USA), followed by staining the nuclei with DAPI. The images for in-situ zymography and vascular density were obtained by confocal microscopy. FIG. 8 shows that MMP-9 inhibition, exogenous MMP-8 treatment, and combined MMP-9 inhibition and exogenous MMP-8 increase angiogenesis as measured by anti-CD31.

Example 3. Pharmaceutical Dosage Forms

The following formulations illustrate representative pharmaceutical dosage forms that may be used for the therapeutic or prophylactic administration of a compound, enzyme, or composition described herein, or a pharmaceutically acceptable salt, solvate, or composition thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |

| (iii) Capsule | mg/capsule |
|---|---|
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100g |

These formulations may be prepared by conventional procedures well known in the pharmaceutical art. It will be appreciated that the above pharmaceutical compositions may be varied according to well-known pharmaceutical techniques to accommodate differing amounts and types of active ingredient(s) 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A therapeutic composition for treating a wound comprising the enzyme MMP-8 and a selective MMP-9 inhibitor, wherein the MMP-9 inhibitor is a compound of Formula XIII or Formula XIV:

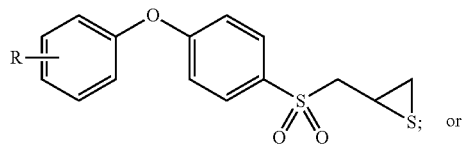
(XIII)

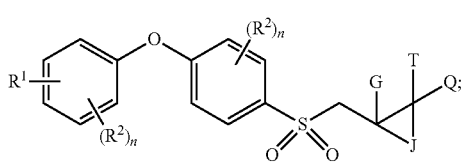
(XIV)

or a salt or solvate thereof;
wherein:
R is H, OH, NH$_2$, NH-amino acid, or —X—(C=O)—R' where X is O or NH, and R' is alkyl, aryl, alkylaryl, amino, or alkoxy, where any alkyl, aryl, or amino is optionally substituted;
R$^1$ is —CH$_2$—NHR$^a$ where R$^a$ is H or (C$_1$-C$_6$)alkanoyl; —NH—C(=NH)—NH$_2$;

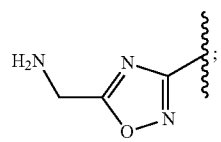 [SMILES: *c1noc(CN)n1]

J is S or O;
G, T, and Q are each independently H, (C$_1$-C$_6$)alkyl, or —CN;
each R$^2$ is independently H, OH, (C$_1$-C$_6$)alkyl, (C$_1$-C$_6$)alkoxy, (C$_1$-C$_6$)alkanoyl, (C$_1$-C$_6$)alkanoyloxy, aryl, heteroaryl, carboxy, cyano, nitro, halo, trifluoromethyl, trifluoromethoxy, SR$^z$, SO$_2$N(R$^z$)$_2$, NR$^z$R$^z$, or COOR$^z$; wherein each R$^z$ is independently H, (C$_1$-C$_6$)alkyl, (C$_1$-C$_6$)alkanoyl, (C$_6$-C$_{10}$)aroyl, aryl, aryl(C$_1$-C$_6$)alkyl, heteroaryl, heteroaryl(C$_1$-C$_6$)alkyl, or optionally a nitrogen protecting group when R$^z$ is covalently bonded to a nitrogen atom; and
each n is independently 0, 1, 2, 3, or 4;
wherein the Ki value of the selective MMP-9 inhibitor for the enzyme MMP-9 is at least 0.5 µM smaller than the Ki value for the enzyme MMP-8; and
wherein the composition comprises the selective MMP-9 inhibitor and the enzyme MMP-8 in a weight ratio of about 10:1 to about 2000:1, and the composition is effective for the exogenous treatment of a wound.

2. The composition of claim 1 wherein the selective MMP-9 inhibitor is selective for the enzyme MMP-9 over the enzyme MMP-8, wherein the Ki value of the MMP-9 inhibitor for the enzyme MMP-9 is at least 2 µM smaller than the Ki value of the MMP-9 inhibitor for the enzyme MMP-8.

3. The composition of claim 1 wherein the MMP-9 inhibitor is:

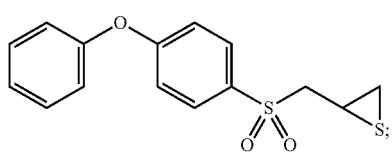

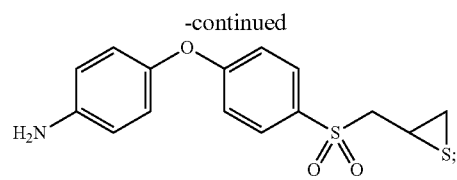

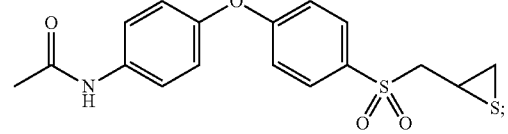

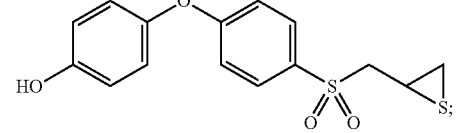

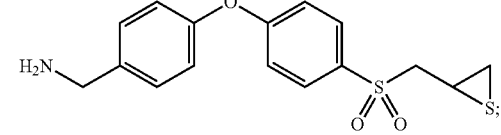

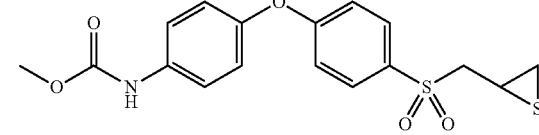

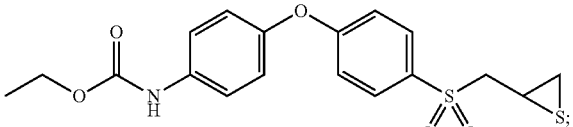

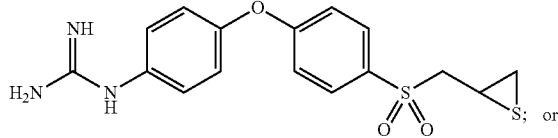

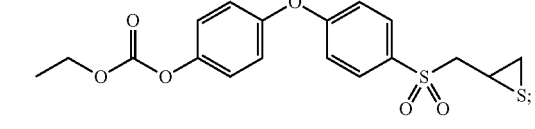

or salt or solvate thereof.

4. The composition of claim 1 wherein the MMP-9 inhibitor is:

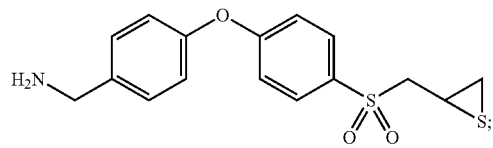
(ND-336)

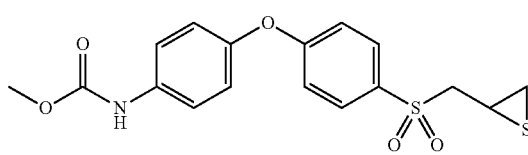
(ND-380)

-continued (ND-394)
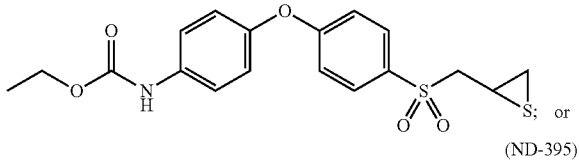 or (ND-395)
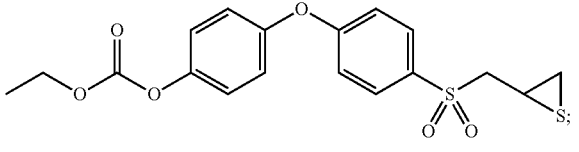

or salt or solvate thereof.

5. The composition of claim 2 wherein the MMP-9 inhibitor is:

(ND-336)
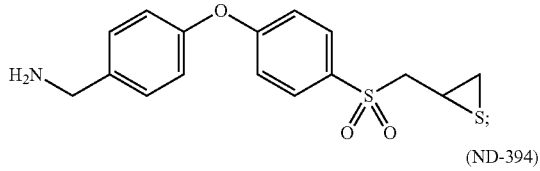

(ND-394)
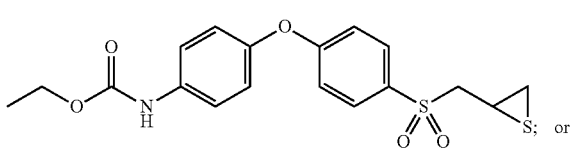 or (ND-395)
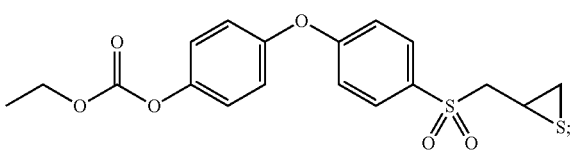

or salt or solvate thereof.

6. The composition of claim 4 wherein the MMP-9 inhibitor is:

(ND-336)
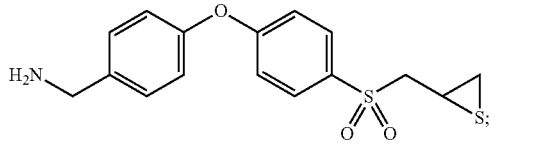

or salt or solvate thereof.

7. The composition of claim 1 in combination with a pharmaceutically acceptable diluent, excipient, or carrier.

8. A method of accelerating the healing of an open wound comprising contacting an open wound in a subject with an effective amount of the composition according to claim 1, thereby accelerating the healing of the wound.

9. The method of claim 8 wherein the open wound is contacted with at least about 0.5 µg of the enzyme MMP-8 per 50 mm² of open wound per day.

10. The method of claim 8 wherein the open wound is contacted with about 0.01 mg to about 1 mg of the selective MMP-9 inhibitor per 50 mm² of open wound per day.

11. The method of claim 10 wherein the MMP-9 inhibitor is:

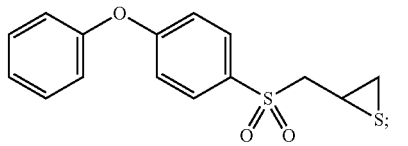

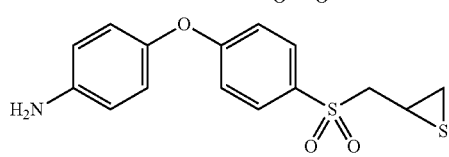

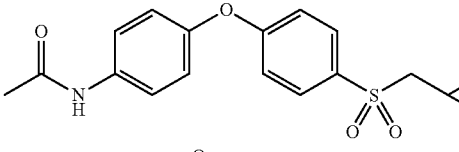

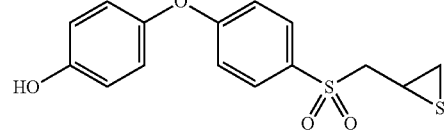

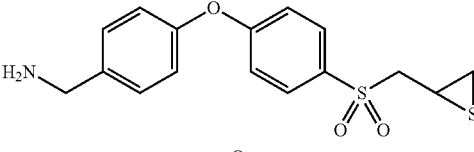

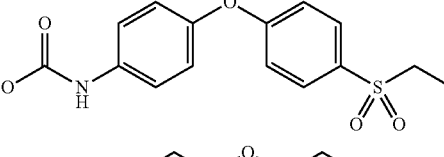

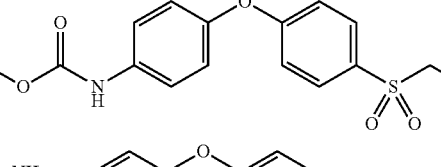

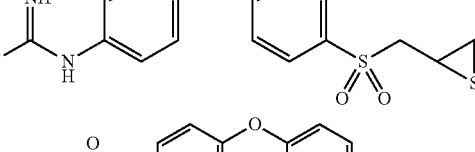 or

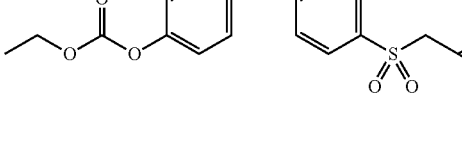

or salt or solvate thereof.

12. The method of claim 10 wherein the selective MMP-9 inhibitor is selective for MMP-9 over MMP-8, wherein the Ki value of the inhibitor for MMP-9 is at least 2 µM smaller than the Ki value of the inhibitor for MMP-8.

13. The method of claim 12 wherein the MMP-9 inhibitor is:

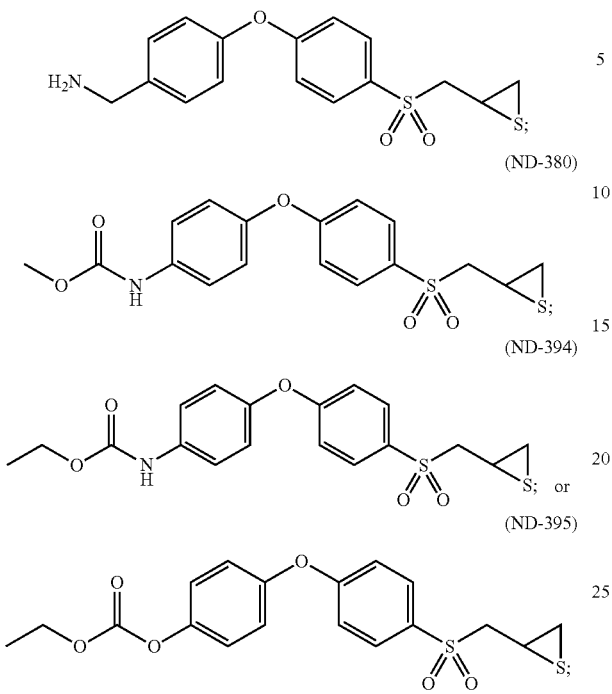

(ND-336)
(ND-380)
(ND-394)
(ND-395)

or salt or solvate thereof.

14. The method of claim 13 wherein the MMP-9 inhibitor is:

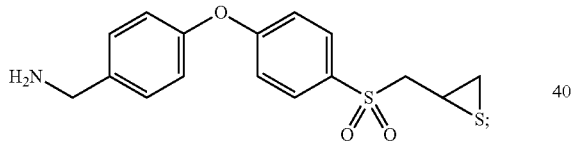

(ND-336)

or salt or solvate thereof.

15. The method of claim 8 wherein at least about 0.05 mg of the selective MMP-9 inhibitor is administered to the subject per 50 mm² of open wound per day.

16. The method of claim 10 wherein the open wound is a chronic wound and the subject is diabetic.

17. A method for decreasing inflammation and increasing angiogenesis in a diabetic wound comprising administering to a subject having a diabetic wound an effective amount of a composition of claim 7.

18. A method for reducing the amount of apoptotic cells in a diabetic wound comprising administering to a subject having a diabetic wound an effective amount of a composition of claim 7.

19. The composition of claim 1 wherein the selective MMP-9 inhibitor is a compound of Formula XIII:

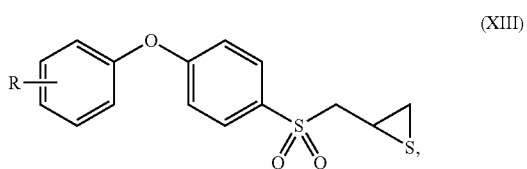

(XIII)

or a salt thereof; wherein:
R is H, OH, NH$_2$, NH-amino acid; or —X—(C=O)—R';
X is O or NH; and
R' is alkyl, aryl, alkylaryl, amino, or alkoxy; wherein any alkyl, aryl, or amino is optionally substituted.

20. The composition of claim 1 wherein the selective MMP-9 inhibitor is a compound of Formula XIV:

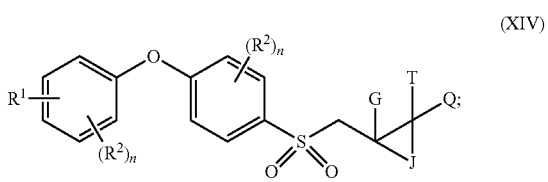

(XIV)

or a salt thereof; wherein:
R$^1$ is —CH$_2$—NHR$^a$ where R$^a$ is H or (C$_1$-C$_6$)alkanoyl; —NH—C(=NH)—NH$_2$; or

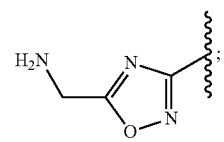 [SMILES: *c1noc(CN)n1]

J is S or O;
G, T, and Q are each independently H, (C$_1$-C$_6$)alkyl, or —CN;
each R$^2$ is independently H, OH, (C$_1$-C$_6$)alkyl, (C$_1$-C$_6$) alkoxy, (C$_1$-C$_6$)alkanoyl, (C$_1$-C$_6$)alkanoyloxy, aryl, heteroaryl, carboxy, cyano, nitro, halo, trifluoromethyl, trifluoromethoxy, SR$^z$, SO$_2$N(R$^z$)$_2$, NR$^z$R$^z$, or COOR$^z$; wherein each R$^z$ is independently H, (C$_1$-C$_6$)alkyl, (C$_1$-C$_6$)alkanoyl, (C$_6$-C$_{10}$)aroyl, aryl, aryl (C$_1$-C$_6$)alkyl, heteroaryl, heteroaryl(C$_1$-C$_6$)alkyl, or optionally a nitrogen protecting group when R$^z$ is covalently bonded to a nitrogen atom; and
B each n is independently 0, 1, 2, 3, or 4.

* * * * *